US012073364B2

(12) United States Patent
Alawi et al.

(10) Patent No.: US 12,073,364 B2
(45) Date of Patent: Aug. 27, 2024

(54) COMPUTER IMPLEMENTED SYSTEM AND ASSOCIATED METHODS FOR MANAGEMENT OF WORKPLACE INCIDENT REPORTING

(71) Applicant: Alawi Global Holdings LLC, Miami Beach, FL (US)

(72) Inventors: Killian Alawi, Bozeman, MT (US); Zubeida Alawi, Bozeman, MT (US)

(73) Assignee: ALAWI GLOBAL HOLDINGS LLC

( * ) Notice: Subject to any disclaimer, the term of this patent is extended or adjusted under 35 U.S.C. 154(b) by 610 days.

(21) Appl. No.: 17/006,321

(22) Filed: Aug. 28, 2020

(65) Prior Publication Data
US 2021/0073736 A1 Mar. 11, 2021

Related U.S. Application Data

(60) Provisional application No. 62/898,539, filed on Sep. 10, 2019.

(51) Int. Cl.
*G06Q 10/105* (2023.01)
*G06F 9/455* (2018.01)
(Continued)

(52) U.S. Cl.
CPC ....... *G06Q 10/105* (2013.01); *G06F 9/45558* (2013.01); *G06F 9/547* (2013.01);
(Continued)

(58) Field of Classification Search
CPC .......... G06Q 10/105; G06Q 10/06315; G06Q 30/0185; G06Q 40/08; G06Q 50/26;
(Continued)

(56) References Cited

U.S. PATENT DOCUMENTS

| | | | |
|---|---|---|---|
| 8,977,842 B1* | 3/2015 | McCorkendale | G06F 21/53 380/285 |
| 2016/0182473 A1* | 6/2016 | Cignetti | G06F 21/44 713/171 |

(Continued)

OTHER PUBLICATIONS

Radwan et al. (Cloud-based Service for Secure Electronic Medical Record Exchange, ICCTA 2012, Oct. 13-15, 2012, pp. 94-103) (Year: 2012).*

(Continued)

*Primary Examiner* — Oleg Korsak
(74) *Attorney, Agent, or Firm* — COLLABORATIVE IP; Paul Ditmyer

(57) ABSTRACT

The computer implemented systems, devices, and methods are for documenting and tracking workplace injuries/incidents, generating safety analytics, providing fraud prevention features, and delivering wellness/training resources, for example. The Workplace Incident Reporting Platform (WIRP) is for industry project managers, associates, insurers, and medical providers. The WIRP is an innovative, user-friendly, secure digital platform that increases efficiency on the job site and brings enterprise leaders, designated employee representatives, associates, and their medical providers together as a team. The WIRP does this by providing a resourceful digital approach to document accurate, and comprehensive, First Report of Injury (FRI). The WIRP's streamline and digitized document record control benefits both the associates and enterprise with smart safety analytics, and updated status reports.

23 Claims, 17 Drawing Sheets

(51) Int. Cl.
    *G06F 9/54*     (2006.01)
    *G06Q 10/0631*     (2023.01)
    *G06Q 30/018*     (2023.01)
    *G06Q 40/08*     (2012.01)
    *G06Q 50/26*     (2012.01)
    *G16H 15/00*     (2018.01)
    *G16H 40/20*     (2018.01)
    *H04L 9/32*     (2006.01)
    *H04L 9/40*     (2022.01)

(52) U.S. Cl.
    CPC ... *G06Q 10/06315* (2013.01); *G06Q 30/0185* (2013.01); *G06Q 40/08* (2013.01); *G06Q 50/26* (2013.01); *G16H 15/00* (2018.01); *G16H 40/20* (2018.01); *H04L 9/3263* (2013.01); *H04L 63/0428* (2013.01); *G06F 2009/45595* (2013.01); *G06Q 2220/00* (2013.01)

(58) Field of Classification Search
    CPC .... G16H 40/20; G16H 15/00; G06F 9/45558; G06F 9/547; H04L 9/3263; H04L 63/0428

See application file for complete search history.

(56) References Cited

U.S. PATENT DOCUMENTS

2018/0159856 A1*   6/2018   Gujarathi ............ H04L 63/0281
2018/0324167 A1*  11/2018   Mathaiyan ............ G06F 9/5072

OTHER PUBLICATIONS

Esteves et al. (On the Management of Virtual Networks, IEEE, Jul. 2013, pp. 80-88) (Year: 2013).*

Chandramouli (Security Recommendations for Server-based Hypervisor Platforms, NIST Special Publication 800-125A, Jun. 2018, 39 pages) (Year: 2018).*

\* cited by examiner

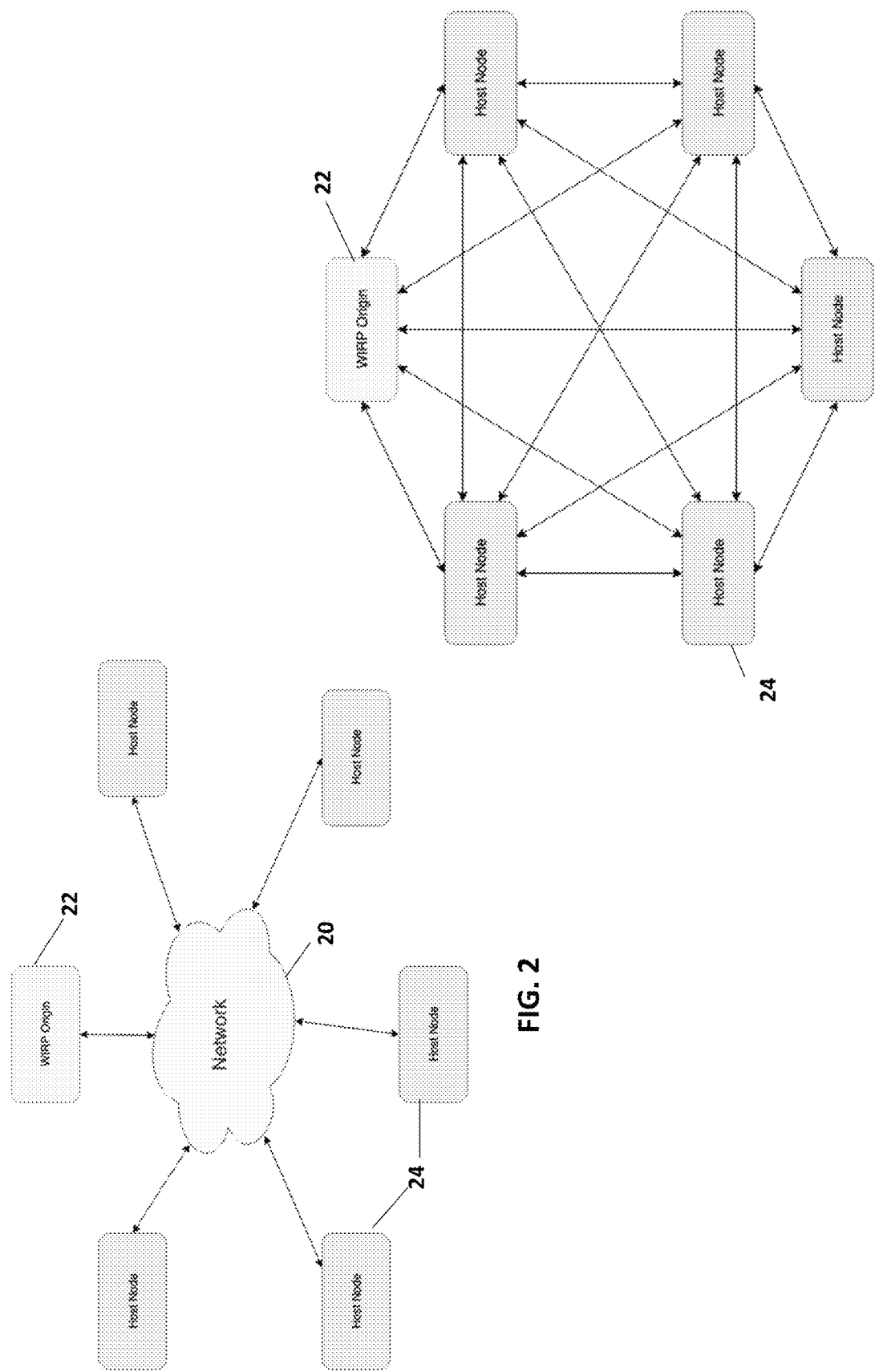

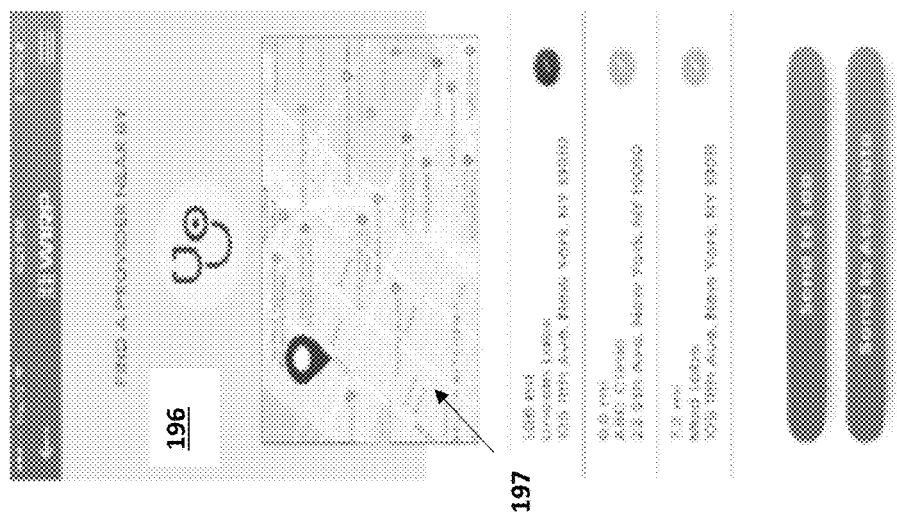
FIG. 19B
FIG. 19A
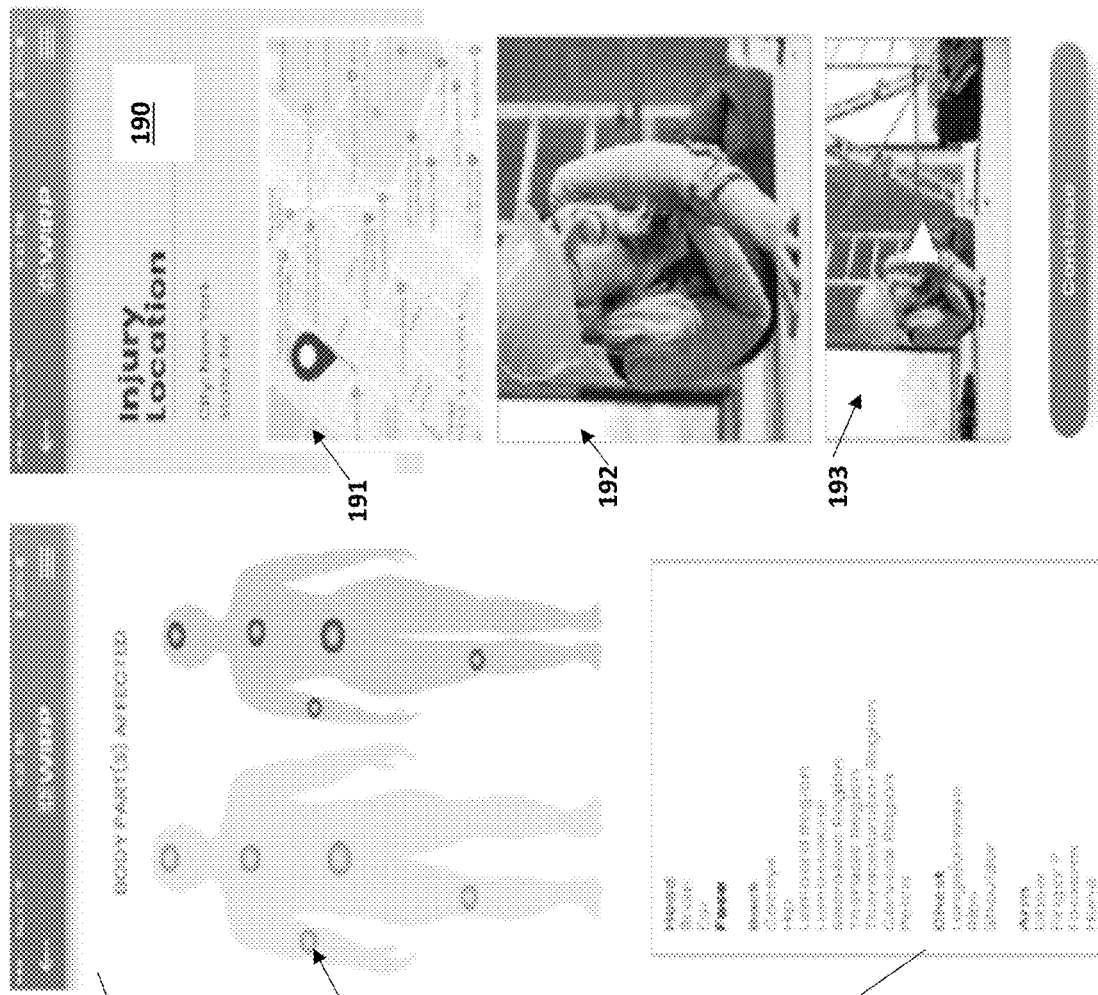
FIG. 18

COMPUTER IMPLEMENTED SYSTEM AND ASSOCIATED METHODS FOR MANAGEMENT OF WORKPLACE INCIDENT REPORTING

RELATED APPLICATIONS

This application claims priority to U.S. Provisional Application Ser. No. 62/898,539 filed Sep. 10, 2020 titled "COMPUTER IMPLEMENTED SYSTEM AND ASSOCIATED METHODS FOR MANAGEMENT OF WORK INJURY REPORTING" which is incorporated herein in its entirety by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to systems, software and methods for reporting, documenting and managing incidents and injuries in the workplace.

BACKGROUND

Currently, workplace incidents/injury reports are documented on paper and stored or reported via individual scanned/faxed forms tracked by the enterprise project manager. The challenges with the current approach include: Incidents and injuries are not being documented efficiently and/or correctly; Papers can be lost or edited after the report is written; There is no way to incorporate images and video into incident or injury report forms or files; There is no comprehensive or user-friendly way to document timely witness statements; There is no comprehensive way to analyze trend reports or reliably identify workplace safety trends; and There is no secure and encrypted database for incident recording or management.

Referring to the flow diagram in FIG. 1, the typical workplace injury reporting process will be described. After an incident, in the QUICK ACTION column, a Designated Employee Representative (DER) responds to urgent medical attention needs, and writes the First Report of Injury (FRI) report on the medical paper form. For the WORKER, an injured worker agrees to treatment and signs permission slips. The DER sends the paper to Medical Provider Office (e.g. Enterprise office, onsite clinic representative, enterprise HR office, or safety officer) or Company, and the DER sends the permission for treatment paper document to the medical provider. Medical Provider conducts treatment, analysis of injury, recordable level analysis, for example, and then sends injured worker to the local medical provider. The worker may be escorted to doctors by the DER or sent directly in a cab, for example, per employee management.

Medical Provider manages the Occupational Safety and Health Administration (OSHA) recordable process and submits files online, and also sends medical status files back to the DER and tracks workers medical recovery progress via email or phone call while the worker completes a medical visit and starts the recovery, takes off work or returns on modified duty after hearing from the DER and HR, and may also submit their own report of injury statement to HR. The DER also tracks medical recovery process via email and phone calls.

Each enterprise typically has internal company rules about managing workers compensation, insurance company claims, recordable process, human resources, and employee assignments. A workers compensation claim investigation is started and each department, worker, and medical provider tracks their own files and makes phone calls to get status updates when needed.

The accuracy of each filed report is cross-referenced by HR, the DER, and the workers compensation manager independently with back-and-forth emails and site visits to determine status. Each step processing time depends on the accuracy of each person's report writing and data entry pace, coupled with the availability of scheduled meeting times.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to systems, devices, software and methods for documenting and tracking workplace injuries/incidents, generating safety analytics, providing fraud prevention features, and delivering wellness/training resources. The Workplace Incident Reporting Platform (WIRP) is for industry project managers, associates, insurers, and medical providers, etc. WIRP is a user-friendly, secure digital platform that increases efficiency on the job site and brings enterprise leaders, designated employee representatives, associates, and their medical providers together as a team. It does this by providing a resourceful digital way to document accurate, and comprehensive, first report of injury (FRI). The WIRP's streamlined and digitized document record control benefits both the associates and enterprise with smart safety analytics, and updated status reports. WIRP brings a user-friendly customized digital resource with smart analytics to streamline the process with recording features and safety focused secure protocols. Used herein, "Workplace" includes any organization (e.g., student bodies, youth athletics, etc.) that involves incident or injury reporting.

Each company may create a secure and encrypted internal WIRP host node and/or network customized to its industry and number of employees. Associates and enterprise workers download the WIRP app (mobile or desktop) and set up a profile and medical ID card based on their individual position and experience. WIRP technology assists with creating profiles, ID cards, and assigns a WIRP ID number to activate secure records key. People become aware of the WIRP from enterprise connections and networks, hiring managers will include the WIRP in the job introduction package, each profile will have a private number and enterprise connection, users engage with medical providers, wellness resources, and safety training guides.

The WIRP is not only a secure platform that brings the medical reporting process from paper into the digital revolution, but as the process and system that can build an industry standard safety protocol. The WIRP brings accurate adoption and proliferation of digital safety record keeping, training, and wellness resources to the individual and into the workplace, encompassing a lifestyle that will transform business techniques. The WIRP method of collection and collation of data enables improvement and efficiency in the prevention of workplace injuries and enables more accurate workers' compensation claim tracking and processing.

In the Associate/worker user experience, the WIRP may act as a wellness resource, safety training database, report generator for (witness statements and personal injury reports), a status update indicator tracking recovery, an assignment indicator, and local medical provider locator features. As for the Enterprise user experience, the WIRP may act as a status communicator between the enterprise and their workers. Some immediate changes that the WIRP users will experience include: Precise, secure and detailed data collection that will assist the loss prevention officer and safety officer; Eliminating the cumbersome and inefficient paper files/records with a digitized secure record on a smart device; Streamline industry report communication; Built-in incentives to use the mobile application regardless of job; and Increase precision and timeliness of incident reporting.

This and other objects, advantages and features in accordance with the present embodiments may be provided by a computer-implemented system, using a client-server model architecture, and operating as a Workplace Incident Reporting Platform (WIRP) for use by multiple user groups including an Enterprise client, a Medical facility, an Individual Associate, and/or an Insurance company. The system includes a WIRP Origin, an Orchestrator, and a Provisioner together defining a data servicing network. The WIRP Origin is configured as a server to run at least three primary services including a container registry, an identification directory, and a certificate authority. The WIRP Origin hosts a private Application Programming Interface (API) configured for internal operations that interact directly with data processing, data validation, data storage, and data management within the data servicing network, and the WIRP Origin hosts a public API configured for providing authorized user groups with external access to the data servicing network.

The Orchestrator is a container orchestration system communicatively coupled to the container registry using the WIRP Origin private API and configured to deploy, manage, store, and scale encrypted containers that contain WIRP data for permissioned access by specific user groups. The Provisioner is a hypervisor that provisions and manages virtual machines, the virtual machines run WIRP host node software to operate as host nodes that process WIRP data into reports, communicate data within the data servicing network utilizing the WIRP Origin private API, communicate with the identification directory in the WIRP Origin, by utilizing the WIRP Origin private API, to authorize users by authenticating user identification, and providing access to the reports via the WIRP Origin public API for an authorized user within a user group of the multiple user groups. The Provisioner communicates with the certificate authority in the WIRP Origin and assigns a cryptographic digital certificate to a respective host node thereby defining a valid host node, the cryptographic digital certificate is a public-key certificate that is issued by the WIRP Origin certificate authority and used to authenticate valid host nodes with respect to an Enterprise client, which grants permissions for encrypted communications between user groups via the WIRP Origin public API, and which grants permissions for encrypted communications between the WIRP Origin, the Orchestrator, and the valid host node via the WIRP Origin private API within the data servicing network.

Additionally and/or alternatively, the Provisioner communicates with the certificate authority in WIRP Origin to assign the cryptographic digital certificate to the host node once a virtual machine is running the WIRP host node software.

Additionally and/or alternatively, valid host nodes are publicly accessible by authorized users in the WIRP network via the WIRP Origin public API; and wherein each host node is configured to process all incoming data from the WIRP Origin public API, and to reject any unauthorized requests.

Additionally and/or alternatively, each host node corresponds to one of an active Enterprise client, Insurance company, and Medical facility.

Additionally and/or alternatively, the encrypted containers include WIRP data repositories, storing the WIRP data relating to each user group, and being managed by the Orchestrator and backed-up by the WIRP Origin container registry.

Additionally and/or alternatively, the WIRP data committed to the repositories is immutable, so that changes to a parent state of a repository require committing the changes with respect to the parent state to create a child state of the repository, which allows authorized users to see a history of changes and updates made to a respective repository. Updates change the saved state of the encrypted container, and saved container state changes are pushed to the WIRP Origin container registry and backed-up as a new version of the container.

Additionally and/or alternatively, the encrypted containers are mounted to corresponding virtual machines that are operating as valid host nodes, so that the WIRP data stored in the mounted containers is available to the valid host node as a storage volume.

Additionally and/or alternatively, changes made to the repositories from the valid host nodes affects the mounted container that includes the respective repository, so that changes made by users to WIRP data in repositories is not saved in the valid host nodes, but rather automatically saved in the mounted containers, thereby allowing the mounted containers to be unmounted from the valid host node and the data still be saved and accessible.

Additionally and/or alternatively, valid host nodes authenticate a user's identity via the WIRP Origin identification directory upon receiving user input data via the WIRP Origin public API, process the user input data based upon a type of submitted form, and then save the processed user input data to the respective repository that is within the encrypted container mounted on the associated valid host node.

Additionally and/or alternatively, each deployed and stored container includes tags that identify a type of WIRP data that is stored in the corresponding container. Branches of a WIRP data repository may utilize a series of tags to allow selected WIRP data to be compartmentalized from other WIRP data. Sub-branches may utilize sub-tags so that a portion of the selected WIRP data can be shared with other user groups.

Additionally and/or alternatively, data processing, data validation, data storage, and data management, within the data servicing network, are automated via the WIRP Origin private API, and requests made from the Enterprise client via the WIRP Origin public API result in automated operations via the WIRP Origin private API including creation of new repositories within encrypted containers, scaling containers, and provisioning new host nodes.

Additionally and/or alternatively, the Orchestrator is configured to push and pull the encrypted containers to and from the WIRP Origin container registry, where the encrypted containers are backed up and version controlled for recovery and scaling. The Orchestrator may be configured to scale the encrypted container's available storage and compute resources based upon the encrypted container operational needs.

Additionally and/or alternatively, valid host nodes process WIRP data into reports including at least one of a first report of Injury (FRI), a witness statement report, a personal incident report, a safety analysis report, an employee modified duty report, a medical clearance report, a workers comp report, an insurance report, a permission for treatment report, a drug screening report, a pandemic illness screening report, and a wellness physical report.

Additionally and/or alternatively, the identification directory of the WIRP Origin securely stores the user identification (ID) of registered users of the user groups so that registered users can securely communicate to other registered users via the corresponding valid host node and the WIRP Origin public API.

Additionally and/or alternatively, the WIRP Origin provides for the communication of WIRP data including videos, images, text, documents, and reports from a registered user to the Medical facility in compliance with health record portability safeguards and government regulations.

Other objects, advantages and features in accordance with the present embodiments may be provided by a computer-implemented system, using a client-server model architecture, and operating as a Workplace Incident Reporting Platform (WIRP) for use by multiple user groups including an Enterprise client, a Medical facility, an Individual Associate, and an Insurance company. The system includes a WIRP Origin, an Orchestrator, and a Provisioner together defining a data servicing network. The WIRP Origin is configured as a server to run at least three primary services including a container registry, an identification directory, and a certificate authority. The WIRP Origin hosts a private Application Programming Interface (API) configured for internal operations that interact directly with data processing, data validation, data storage, and data management within the data servicing network. The WIRP Origin hosts a public API configured for providing authorized user groups with external access to the data servicing network.

The Orchestrator is a container orchestration system communicatively coupled to the container registry using the WIRP Origin private API and configured to deploy, manage, and store encrypted containers that contain WIRP data for permissioned access by specific user groups. The WIRP Origin provides for the communication of WIRP data including videos, images, text, documents, and reports from a registered user of the user groups to the Medical facility in compliance with health record portability safeguards and government regulations. The Provisioner is a hypervisor that provisions and manages virtual machines, the virtual machines run WIRP host node software to operate as host nodes that process WIRP data, communicate data within the data servicing network utilizing the WIRP Origin private API, communicate with the identification directory to authorize users by authenticating user identification, and providing access to the WIRP data via the WIRP Origin public API for an authorized user within a user group of the multiple user groups. Each host node corresponds to one of an active Enterprise client, Insurance company, and Medical facility.

Valid host nodes process WIRP data into reports including at least one of a First Report of Injury (FRI), a witness statement report, a personal incident report, a safety analysis report, an employee modified duty report, a medical clearance report, a workers comp report, an insurance report, a permission for treatment report, a drug screening report, a pandemic illness screening report, and a wellness physical report. The Provisioner communicates with the certificate authority and assigns a cryptographic digital certificate to a respective host node thereby defining a valid host node with respect to an Enterprise client, which thereby grants permissions for encrypted communications between user groups via the WIRP Origin public API, and which grants permissions for encrypted communications between the WIRP Origin, the Orchestrator, and the valid host node via the WIRP Origin private API within the data servicing network.

Additionally and/or alternatively, the Provisioner communicates with the certificate authority in WIRP Origin to assign the cryptographic digital certificate to the host node once a virtual machine is running the WIRP host node software. The valid host nodes are publicly accessible by authorized users in the WIRP network via the WIRP Origin public API. And, each host node is configured to process all incoming data from the WIRP Origin public API, and to reject any unauthorized requests.

Additionally and/or alternatively, the encrypted containers include WIRP data repositories, storing the WIRP data relating to each user group, and being managed by the Orchestrator and backed-up by the WIRP Origin container registry.

Additionally and/or alternatively, the WIRP data committed to the repositories is immutable, so that changes to a parent state of a repository require committing the changes with respect to the parent state to create a child state of the repository, which allows authorized users to see a history of changes and updates made to a respective repository.

Additionally and/or alternatively, updates change the saved state of the encrypted container, and saved container state changes are pushed to the WIRP Origin container registry and backed-up as a new version of the container.

Additionally and/or alternatively, the encrypted containers are mounted to corresponding virtual machines that are operating as valid host nodes, so that the WIRP data stored in the mounted containers is available to the valid host node as a storage volume.

Additionally and/or alternatively, changes made to the repositories from the valid host nodes affects the mounted container that includes the respective repository, so that changes made by users to WIRP data in repositories is not saved in the valid host nodes, but rather automatically saved in the mounted containers, thereby allowing the mounted containers to be unmounted from the valid host node and the data still be saved and accessible.

Additionally and/or alternatively, valid host nodes authenticate a user's identity via the WIRP Origin identification directory upon receiving user input data via the WIRP Origin public API, process the user input data based upon a type of submitted form, and then save the processed user input data to the respective repository that is within the encrypted container mounted on the associated valid host node.

Additionally and/or alternatively, each deployed and stored container includes tags that identify a type of WIRP data that is stored in the corresponding container. Branches of a WIRP data repository may utilize a series of tags to allow selected WIRP data to be compartmentalized from other WIRP data. Sub-branches may utilize sub-tags so that a portion of the selected WIRP data can be shared with other user groups.

Additionally and/or alternatively, data processing, data validation, data storage, and data management, within the data servicing network, are automated via the WIRP Origin private API, and requests made from the Enterprise client via the WIRP Origin public API result in automated operations via the WIRP Origin private API including creation of new repositories within encrypted containers, scaling containers, and provisioning new host nodes.

Additionally and/or alternatively, the Orchestrator is configured to push and pull the encrypted containers to and from the WIRP Origin container registry, where the encrypted containers are backed up and version controlled for recovery and scaling; and wherein the Orchestrator is configured to scale the encrypted container's available storage and compute resources based upon the encrypted container operational needs.

BRIEF DESCRIPTION OF THE DRAWINGS

FIG. 2 is a schematic diagram illustrating an example network topology for the Workplace Incident Reporting Platform (WIRP) in accordance with features of the present invention.

FIG. 3 is a schematic diagram illustrating an example of network communication for the WIRP in accordance with features of the present invention.

FIG. 18 is a schematic screenshot illustrating an example of the mobile application user interface including a body map for incident reporting within the WIRP in accordance with features of the present invention.

FIGS. 19A and 19B are schematic screenshots illustrating an example of the mobile application user interface including a geolocation map for incident reporting within the WIRP in accordance with features of the present invention.

DETAILED DESCRIPTION OF THE INVENTION

Figure 1:
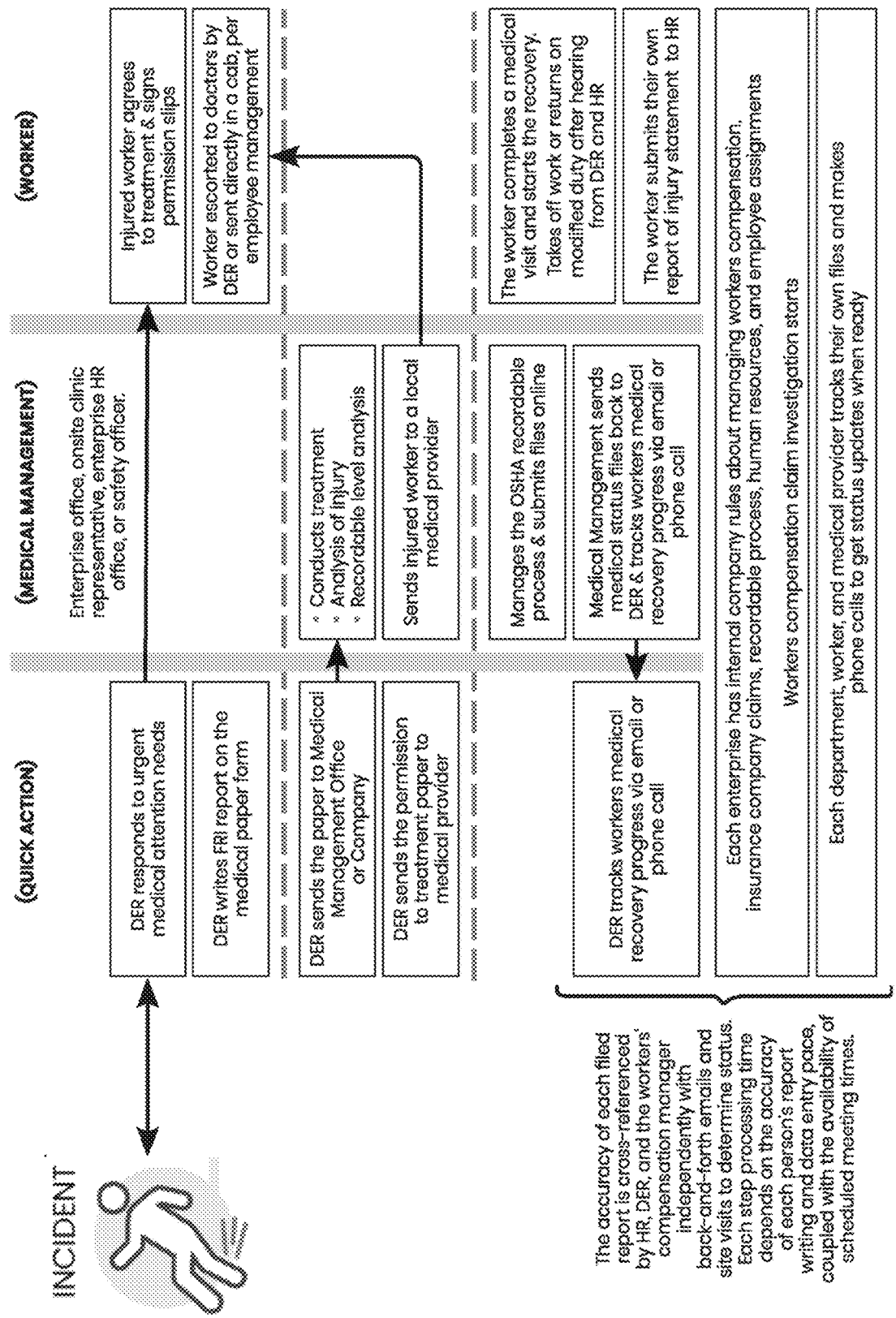
FIG. 1 is a flow diagram illustrating a conventional workplace injury reporting process.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Before describing the present disclosure in detail, it is to be understood that this disclosure is not limited to parameters of the particularly exemplified systems, methods, apparatus, products, processes, and/or kits, which may, of course, vary. It is also to be understood that the terminology used herein is only for the purpose of describing particular embodiments of the present disclosure, and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary embodiments or implementations. As used herein, the terms "embodiment," "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "sensor" includes one, two, or more sensors.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering (e.g., element "10" and element "210.") Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein.

It is also noted that systems, methods, apparatus, devices, products, processes, compositions, and/or kits, etc., according to certain embodiments of the present invention may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

In cryptography and computer science, a hash tree or Merkle tree is a tree in which every leaf node is labelled with the hash of a data block, and every non-leaf node is labelled with the cryptographic hash of the labels of its child nodes. Hash trees allow efficient and secure verification of the contents of large data structures. Hash trees are a generalization of hash lists and hash chains.

Demonstrating that a leaf node is a part of a given binary hash tree requires computing a number of hashes proportional to the logarithm of the number of leaf nodes of the tree; this contrasts with hash lists, where the number is proportional to the number of leaf nodes itself. The concept of hash trees is named after Ralph Merkle who patented it in 1979.

Hash trees can be used to verify any kind of data stored, handled and transferred in and between computers. They can help ensure that data blocks received from other peers in a peer-to-peer network are received undamaged and unaltered, and even to check that the other peers do not lie and send fake blocks.

Hash trees are used in hash-based cryptography. Hash trees are also used in the IPFS, Btrfs and ZFS file systems (to counter data degradation); Dat protocol; Apache Wave protocol; Git and Mercurial distributed revision control systems; the Tahoe-LAFS backup system; Zeronet; the Bitcoin and Ethereum peer-to-peer networks; the Certificate Transparency framework; and a number of NoSQL systems such as Apache Cassandra, Riak, and Dynamo. Suggestions have been made to use hash trees in trusted computing systems.

A hash tree is a tree of hashes in which the leaves are hashes of data blocks in, for instance, a file or set of files. Nodes further up in the tree are the hashes of their respective children. For example, in the picture hash 0 is the result of hashing the concatenation of hash 0-0 and hash 0-1. That is, hash 0=hash(hash 0-0||hash 0-1) where || denotes concatenation.

Most hash tree implementations are binary (two child nodes under each node) but they can just as well use many more child nodes under each node.

Usually, a cryptographic hash function such as SHA-2 is used for the hashing. If the hash tree only needs to protect against unintentional damage, unsecured checksums such as CRCs can be used.

In the top of a hash tree there is a top hash (or root hash or master hash). Before downloading a file on a P2P network, in most cases the top hash is acquired from a trusted source, for instance a friend or a web site that is known to have good recommendations of files to download. When the top hash is available, the hash tree can be received from any non-trusted source, like any peer in the p2p network. Then, the received hash tree is checked against the trusted top hash, and if the hash tree is damaged or fake, another hash tree from another source will be tried until the program finds one that matches the top hash.

The main difference from a hash list is that one branch of the hash tree can be downloaded at a time and the integrity of each branch can be checked immediately, even though the whole tree is not available yet. For example, in the picture, the integrity of data block L2 can be verified immediately if the tree already contains hash 0-0 and hash 1 by hashing the data block and iteratively combining the result with hash 0-0 and then hash 1 and finally comparing the result with the top hash. Similarly, the integrity of data block L3 can be verified if the tree already has hash 1-1 and hash 0. This can be an advantage since it is efficient to split files up in very small data blocks so that only small blocks have to be re-downloaded if they get damaged. If the hashed file is very big, such a hash tree or hash list becomes fairly big. But if it is a tree, one small branch can be downloaded quickly, the integrity of the branch can be checked, and then the downloading of data blocks can start.

A blockchain is a distributed database that may be used as a distributed ledger including one or more data records storing one or more individual transactions or smart contracts. Generally, distributed ledgers are a shared, replicated, and permissioned ledger that acts as a system of record for businesses. Distributed ledgers provide unique characteristics that can be leveraged for recording transactions and/or contracts including conditions for transactions to occur. Moreover, distributed ledgers may also be used for enforcement of contractual agreements including verification and/or confirmation of performance of contract stipulations.

As used herein, the term "blockchain" generally refers to an open and distributed public ledger comprising a growing list of records, which are linked using cryptography. By design, the blockchain is resistant to modification of the data. The blockchain can include an auditable database that provides a distributed, replicated ledger of cryptographically certified artifacts whose contents are extremely difficult to tamper with without detection, and therefore, are with very high probability, true copies of the intended content, and whose content are open for inspection via a suitable query interface.

As used herein, the term "block" generally refers to a record that is kept in a blockchain. For example, each block contains a cryptographic hash of the previous block, a timestamp, and transaction data, which can generally be represented as a Merkle tree root hash.

Occupational Medicine, until 1960 called industrial medicine, is the branch of medicine which is concerned with the maintenance of health in the workplace, including prevention and treatment of diseases and injuries, with secondary objectives of maintaining and increasing productivity and social adjustment in the workplace. It is, thus, the branch of clinical medicine active in the field of occupational health and safety. OM specialists work to ensure that the highest standards of occupational health and safety are achieved and maintained in the workplace. While OM may involve a wide number of disciplines, it centers on preventive medicine and the management of incident, illness, injury, and disability related to the workplace. Occupational physicians must have a wide knowledge of clinical medicine and be competent in a number of important areas. They often advise international bodies, governmental and state agencies, organizations and trade unions. There are contextual links to physical medicine and rehabilitation and to insurance medicine.

Medical management or Medical Provider are umbrella terms that encompasses the use of IT for health, disease, care and case management functions. Medical management strategies are designed to modify consumer and provider behavior to improve the quality and outcome of healthcare delivery.

Productivity software (also called personal productivity software or office productivity software) is application software used for producing information (such as documents, presentations, worksheets, databases, charts, graphs, digital paintings, electronic music and digital video).

EHR or electronic health record are digital records of health information. They contain all the information you'd find in a paper chart—and a lot more. EHR include past medical history, vital signs, progress notes, diagnoses, medications, immunization dates, allergies, lab data and imaging reports. They can also contain other relevant information, such as insurance information, demographic data, and even data imported from personal wellness devices.

Workplace Incident Reporting Platform (WIRP)

A detailed description of the system, devices, software, user experience and associated methods of the Workplace Incident Reporting Platform (WIRP) follows with reference to FIGS. 2-19. The system and/or method defines rules and interfaces that allow multiple able and related parties to transmit information amongst themselves using computing devices over a network (e.g., the Internet or private intranet). These rules allow for the security and integrity of transmitted data to be made certain by all parties, while following government standards, such as those laid out by the Occupational Safety and Health Administration (OSHA), as well as technical safeguards proclaimed in the Health Insurance Portability and Accountability Act (HIPAA) of 1996, for example.

The WIRP approach will address the problems in incident or injury reporting and the Worker's Compensation Claim industry for injured associates, employers, health care providers, and the insurance industry. WIRP will enable data collection and collation from all industry stakeholders, and provide the vehicle to process the critically valuable data sets from all customers into organized, usable, analytic segments for analysis. This analysis will reduce both cost and loss, reduce fraudulent claims, enhance and speed up workplace safety adjustments, and improve productivity.

WIRP is for enterprise managers, leadership, and designated employee/contractor representatives (e.g. industry project managers), associates, and medical providers, for example, who need to document and track workplace injuries/incidents, who seek to benefit from safety analytics, fraud prevention features, and wellness/training resources. WIRP is an innovative, user-friendly, secure digital platform that increases efficiency on the job site and brings enterprise leaders, designated employee representatives, associates, and their medical providers together as a team. It does this by providing a resourceful digital way to document accurate, and comprehensive, workplace reports such as First Report of Injury (FRI), medical incident reports, witness statements, safety reports, and other industry relevant documentation and reports. WIRP's streamlined and digitized document record control benefits both the associates and enterprise with smart safety analytics, and updated status reports.

Unlike the current workplace injury reporting processes documented on paper files (that does not exist in digital form), WIRP brings a user-friendly customized digital resource with smart analytics to streamline the FRI process with 'just-in-time' recording features and safety focused secure protocols.

Each company may create a secure and encrypted internal WIRP network customized to its industry and number of employees. All associates and enterprise workers may download the WIRP application and set up a profile and medical ID card based on their individual position and experience. WIRP technology assists with creating profiles, ID cards, and assigns a WIRP ID number to activate secure records keys via a cryptographic key exchange. People become aware of WIRP from enterprise connections and networks, hiring managers will include WIRP in the job introduction package, each profile may have a private number and enterprise connection, users engage with medical providers, wellness resources, and safety training guides.

Figure 4:
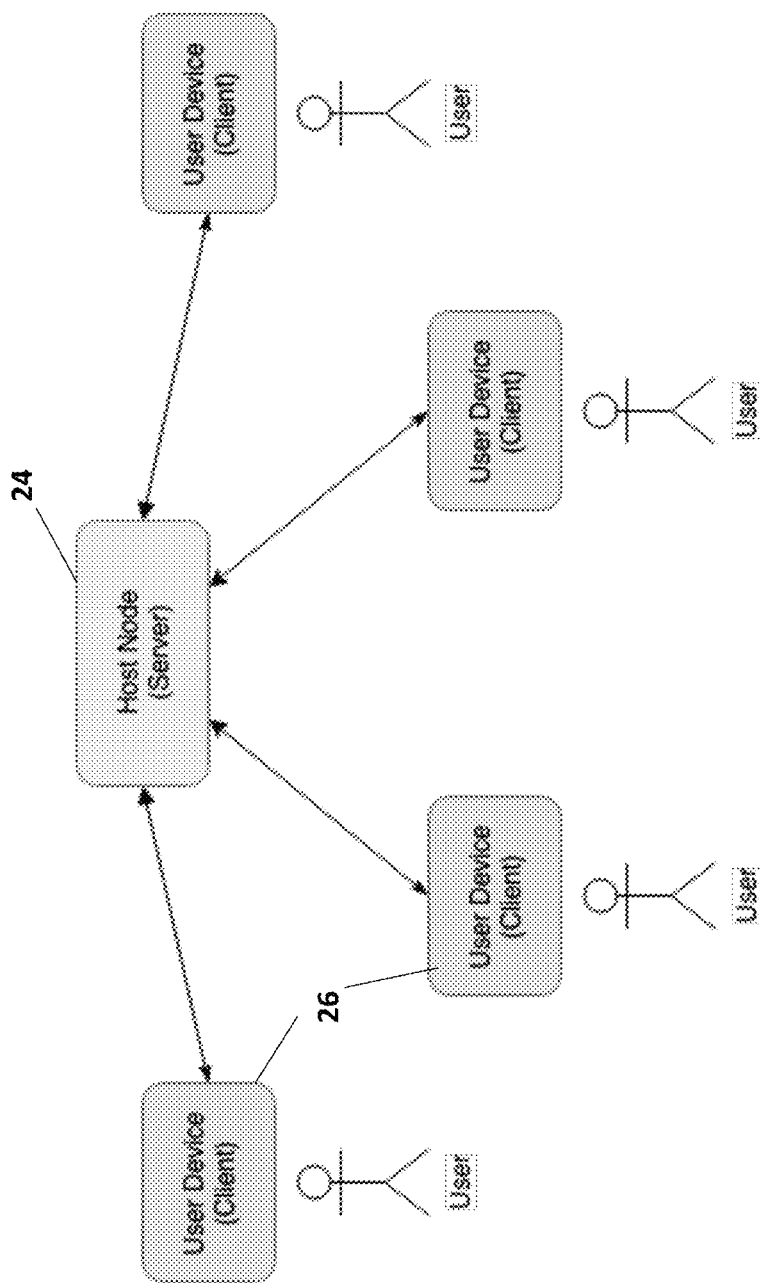
FIG. 4 is a schematic diagram illustrating an example of the server-client architecture for the WIRP in accordance with features of the present invention.

A further description of user experiences and architectural operations is set forth below with reference to the schematic diagrams (FIGS. 2-6). The system and/or method defines rules and interfaces that allow multiple able and related parties to transmit information amongst themselves using computing devices over a network (e.g., the Internet or private intranet). FIG. 2 is a schematic diagram illustrating an example network topology for the WIRP. The network 20 includes WIRP Origin Server 22 (described in detail below) and various host nodes 24 communicatively connected via a wired and/or wireless network. FIG. 3 is a schematic diagram illustrating an example of network communication for the WIRP. FIG. 4 is a schematic diagram illustrating an example of the server-client architecture for the WIRP including a host node 24 and various user devices 26 (clients).

The WIRP system 50 (FIG. 5) preferably includes four user groups: The Enterprise client 52, the Medical facility 54, the Individual Associate user 56, and the Insurance company 58, as illustrated. The computer devices are illustrated as singular users within the respective groups (for ease of explanation), but multiple users within the groups are contemplated. Of course, other or additional user groups (e.g. workers comp, etc.) may also be included, or fewer user groups may operate within the WIRP system 50. The Enterprise client user group 52 is for businesses that have at least one employee. The business is usually required to, or would like to, file incident reports, witness statements, and manage insurance, safety, and health data. The Medical facility user group 54 will communicate with the Enterprise, Insurance, and Individual Associate user groups on specific medical request and search queries. The Individual Associate user group 56 is for employees, non-employees, independent contractors, or other singular users, who want to use the WIRP platform for incident reports. The Insurance user group 58 will act as an analytics platform (e.g. a one-way analytics platform) that produces stripped, concealed, or otherwise anonymized data reports.

Figure 5:
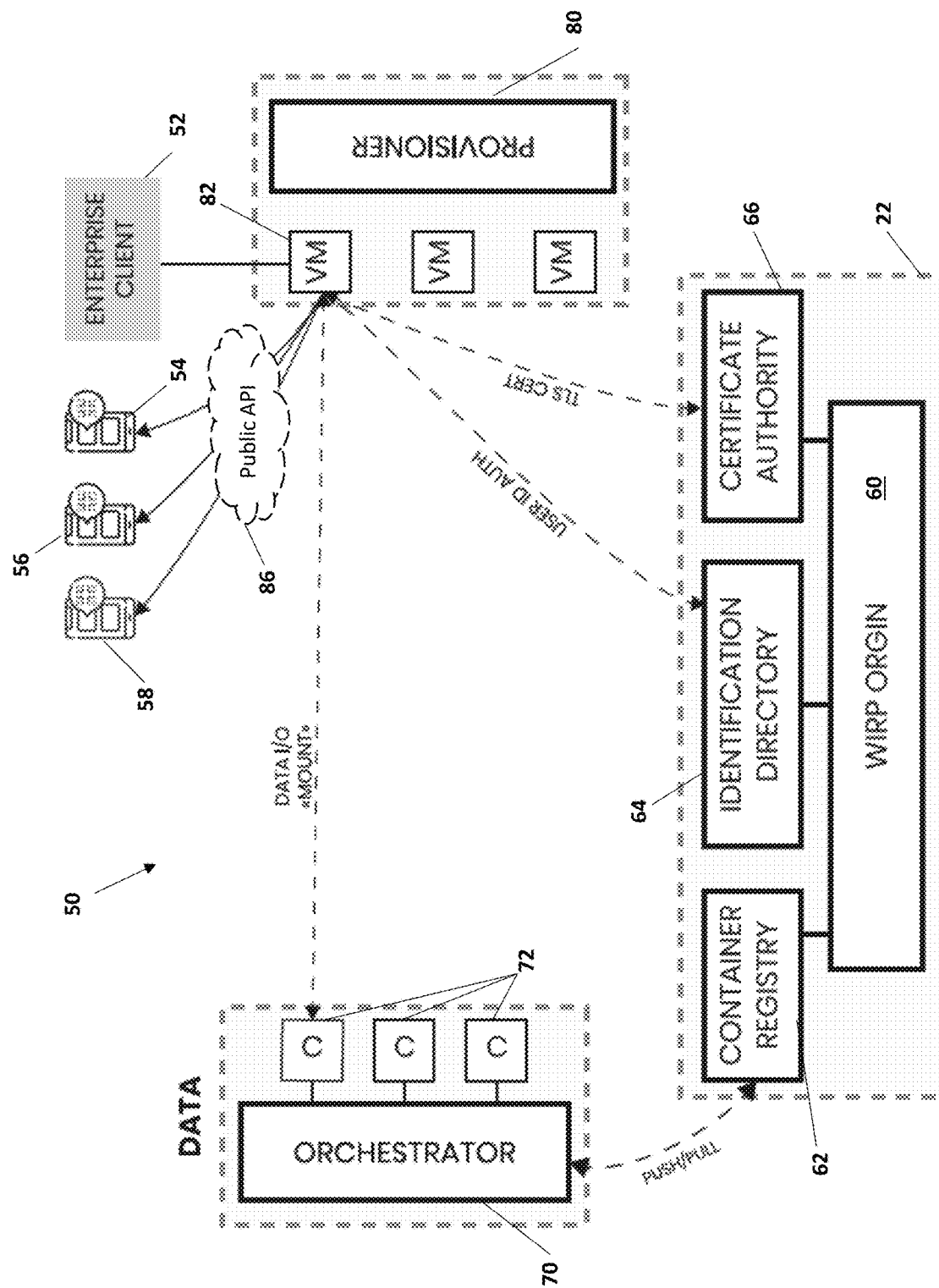
FIG. 5 is a schematic diagram illustrating an embodiment of the computer-implemented system and network of the WIRP in accordance with features of the present invention.

The WIRP system 50 (e.g., software, firmware, hardware) includes a "WIRP Origin" 60 defined in the primary server 22, expanded to a data center, that runs three primary services. The first service being a container registry service 62, the second an identification directory service 64, and the third a certificate authority service 66, as seen in FIG. 5.

The WIRP Origin 60 hosts a private application programming interface (API) 84 that allows for internal operations that interact directly with data processing, validation, storage, and management within a data servicing network that includes an Orchestrator 70 and a Provisioner 80. So, the Orchestrator 70, and the Provisioner 80 may also define data center elements. The Orchestrator 70 is a container orchestration system, which communicates to the container registry 62 using the WIRP Origin private API 84 to, for example, deploy, manage, store, and scale containers 72 that contain the platform's data. These containers 72 will be encrypted since they will be mounted to remote virtual machine servers 82 and the data may be highly sensitive. By compartmentalizing data into encrypted containers 72, the data can be permissioned in a way where only certain users will have the ability to access that data to prevent risk relating to data leakage or breaches.

So, the Orchestrator 70 is communicatively coupled to the container registry 62 using the WIRP Origin private API 84 and configured to deploy, manage, store, and scale encrypted containers 72 that contain WIRP data for permissioned access by specific user groups. The Orchestrator 70 can push and pull these containers 72 to and from the WIRP Origin container registry 62, where the encrypted containers 72 are backed up and version controlled for possible scaling or recovery. Multiple containers 72 can be deployed and run simultaneously, programmable event triggers can update multiple containers 72 asynchronously, and the Orchestrator 70 can scale the container's available storage and compute resources based on what the container 72 needs to operate. These containers 72 will primarily be running working repositories, described in further detail below.

With additional reference to FIGS. 6-9, the Provisioner 80 is a hypervisor or virtualization system that provisions virtual machines 82 of various sizes and manages them for scaling. The virtual machines 82 then run or render WIRP Host Node Software 83 to operate as the host nodes 24, which allows them to properly communicate in the network 20 and send data that utilizes the WIRP Origin's private API 84 while also being publicly accessible via a public API 86 for users. The WIRP Origin 60 hosts the public API 86 configured for providing authorized user groups with external access to the data servicing network. Once a virtual machine 82 is running as a host node 24, the Provisioner 80 connects to the certificate authority 66 in WIRP Origin 60 and assigns a new cryptographic digital certificate 88 (e.g., a WIRP Certificate) to the host node 24. The cryptographic digital certificate 88 may be a public-key certificate that is issued by the WIRP Origin certificate authority 66 and used to authenticate valid host nodes with respect to an Enterprise client 52. The digital certificate 88 may be an extended X.509 public-key certificate, for example, that is issued by the WIRP Origin 60 certificate authority 66 and used to authenticate valid host nodes with respects to Enterprise clients 52. The digital certificates 88 grant permissions for encrypted communications between user groups and other servers within the data servicing network via the WIRP Origin 60 public API 86. The digital certificates 88 grant permissions for encrypted communications between the WIRP Origin 60, the Orchestrator 70, and the valid host node via the WIRP Origin private API 84.

The Provisioner 80 communicates with the identification directory 64 in the WIRP Origin 60, by utilizing the WIRP Origin private API 84, to authorize users by authenticating user identification, and providing access to the WIRP data via the WIRP Origin public API 86 for an authorized user within a user group of the multiple user groups 52, 54, 56 and 58. The Provisioner 80 communicates with the certificate authority 66 in the WIRP Origin 60 and assigns a cryptographic digital certificate 88 to a respective host node 24 thereby defining a valid host node. An invalid cryptographic digital certificate 89 (e.g. expired) will result in the rejection of data processes for such a host node (e.g. FIG. 8).

A host node 24 is a computer operating in both the client-server and the peer-to-peer networking topology models simultaneously. Each host node 24 is a participant and peer in a network 20 of other host nodes, where each host node 24 is owned by an authenticated entity that intends to transact, send, receive, and store WIRP data and information relating to occupational incidents and injuries, e.g., in the workplace. Such entities and classes for a host node 24 would include an Enterprise client 52 or employer, medical facility 54 or medical clinics, insurance companies 58, and a singular network authenticator that is WIRP Origin 60. The WIRP Origin 60 is the originator and manager of cryptographic certificates for each host node 24, where these certificates are utilized to authenticate the identity of a host node 24 and validate that identity to a registered legal entity amongst the previously stated users or classes. In this peer-to-peer network 20 of host nodes 24, each peer acts without a master as both a client of data from peers and the server of data to peers. The WIRP Origin 60 is called upon by peers when they are first setting up their host node 24, updating their host node 24, or initiating a cryptographic handshake to establish secure communications between other host nodes. The role of WIRP Origin 60 may be analogous to a telephone directory, or yellow pages, and a telephone switchboard, where internal communications between peers may not be observed, monitored, or recorded by WIRP Origin.

All host nodes 24 act as the central server and repository of data for their subordinate users, where those users may be the employees of the company that their host node 24 represents on the network 20. Each user on or of a host node 24 is expected to have a personal or mobile computing device with network (e.g. Internet) access, such as a smartphone, where this device allows them to send data to and receive data from their configured employer's host node 24. This follows a client-server network model, where the users' devices act as the client and the host node 24 is the server. It might be deemed best practice to have the host node 24 of a company be on site, while the alternative is for that company to outsource servers to run their host node, which includes the WIRP Enterprise hosting.

Thus, once a host node 24 is fully operational with a valid WIRP Certificate, it can be publicly accessible by active users in the WIRP data servicing network via the use of a public WIRP API, as each host node 24 corresponds to an active Enterprise client 52, Insurance company 58, or Medical facility 54. The data relating to each entity is stored in working repositories within encrypted containers 72 that are managed by the Orchestrator 70 and backed-up by the WIRP Origin container registry 62. These encrypted containers 72 are mounted to the corresponding virtual machines 82 that are operating as host nodes, which means the data in the mounted containers 72 becomes available to the host node virtual machines 82 as a storage volume. This allows for the host nodes to use the encrypted containers 72 and the working data repositories within them as if they were an external hard drive, for example. All changes made to the repository from the host node virtual machines 82 affects the mounted container 72 with that repository being inside of it, so all changes made to any data and documentation inside a repository by users is not saved in the host nodes virtual machine 82, but rather on the mounted containers 72 automatically. This allows the containers 72 to be unmounted from the host node virtual machines 82 and the data still be saved and accessible. As new data enters a container 72, those updates change the state of the container 72, and those container state changes can be pushed to the WIRP Origin container registry 62 and backed-up as a new version of the container 72.

Figure 6B:
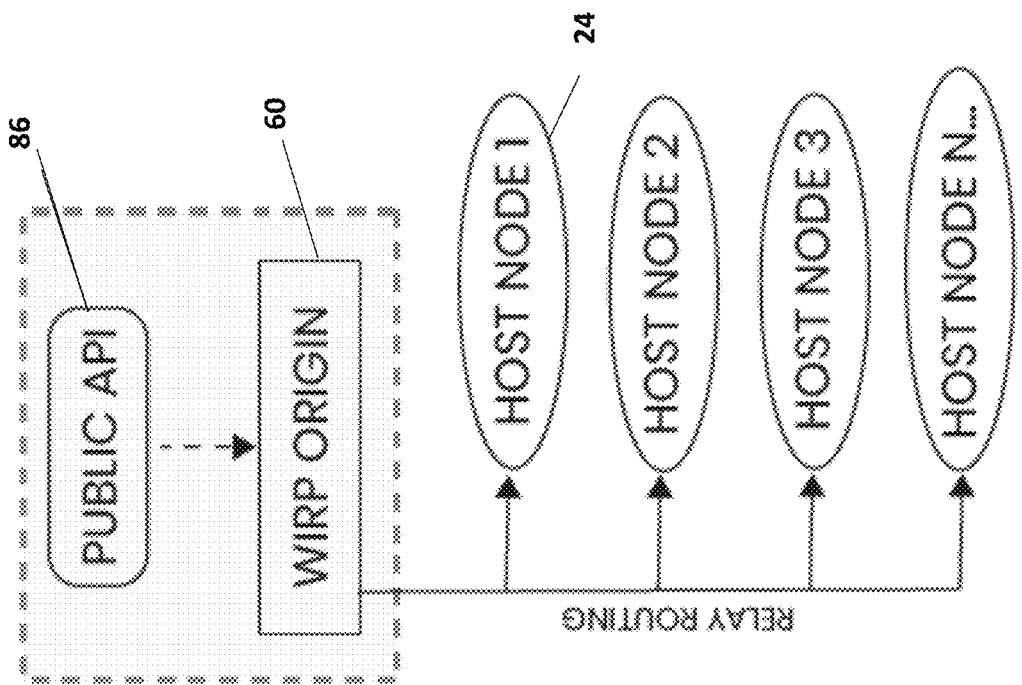
FIG. 6B is a schematic diagram illustrating WIRP data communication with the WIRP Origin public API in accordance with features of the present invention.
Figure 6A:
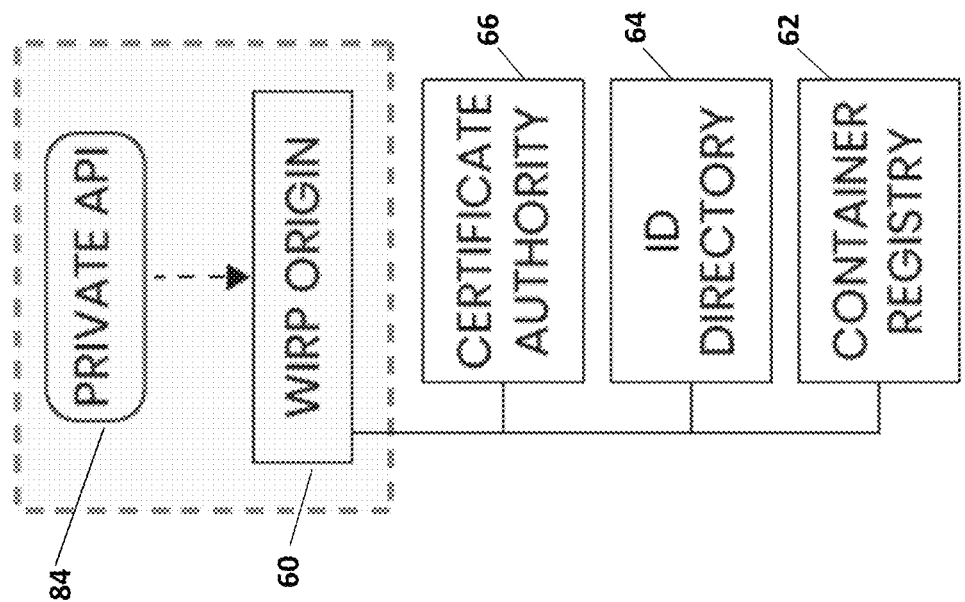
FIG. 6A is a schematic diagram illustrating WIRP data communication with the WIRP Origin private API in accordance with features of the present invention.
Figure 7:
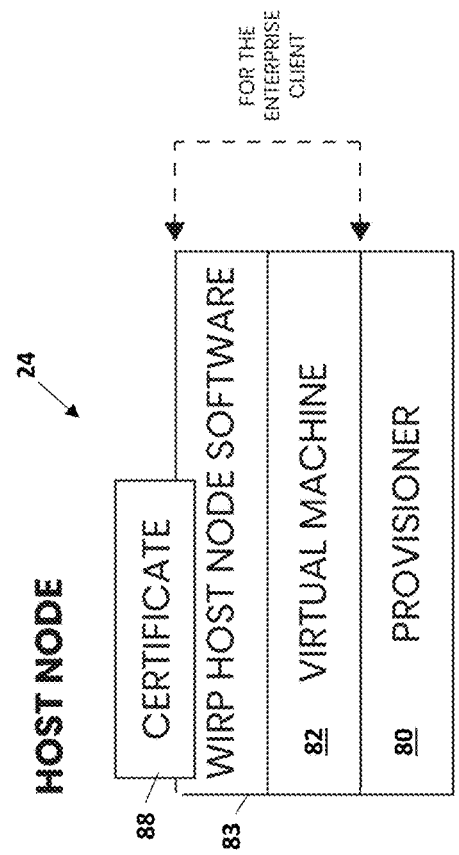
FIG. 7 is a schematic diagram illustrating an example host node for the Enterprise client in accordance with features of the present invention.

Referring additionally to FIGS. 6A and 6B, the WIRP Origin 60 provides for two APIs: a private API 84 for internal data operations, and a public API 86 for users to interact with data. Each valid host node 24 makes data accessible to authorized users via the public API 86. Processes between WIRP Origin 60, the Orchestrator 70, and the Provisioner 80 are extracted into and automated from the private API 84, where requests made from Enterprise client 52 representatives to the private API 84 can conduct large computational operations, such as creating new working repositories, scaling containers 72, and provisioning new host nodes 24.

For example, when Grocery Store A joins the WIRP, a request is sent to WIRP Origin 60, and after receiving this formatted request, WIRP Origin 60 and the Provisioner will automatically provision a new virtual machine 82, the virtual machine will then automatically install and run the software, and it will be assigned a TLS certificate from the WIRP Origin's certificate authority, meaning that virtual machine 82 is now a new valid host node 24 for Grocery Store A. After this process, the enterprise company management will be able to start entering employee details and create WIRP ID cards. The first action of employee data profile entry will add Grocery Store A to the WIRP Origin identification directory 64, which means the certificate authority 66 has that corresponding new business as an identifier and each person/employee added will also have their employee identifier in there. The data movement may be as follows: WIRP Origin→Phone App (Employee ID)→ (to find the virtual machine for incident)→client sends report or report received by host node→published on WIRP public API. At the front end (i.e., the public API 86), an Employee creates an incident form and submits it to the WIRP data servicing network or back end.

Figure 8:
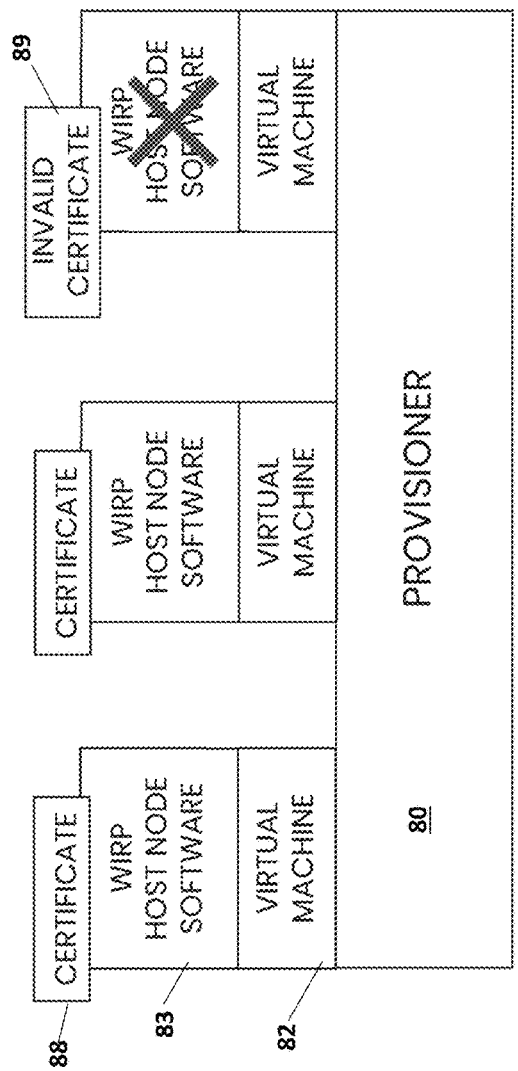
FIG. 8 is a schematic diagram illustrating an example multi-host node arrangement in accordance with features of the present invention.

When an Individual Associate working for a WIRP Enterprise client submits a form (e.g., a witness statement or personal incident form) through the WIRP mobile application, the form (i.e., WIRP data) is sent as a message request with a payload of data to the WIRP public API 86. The message request is routed to the corresponding host node 24 of the corresponding Enterprise client 52. The WIRP platform includes an automated data transfer process while recognizing the user that is sending the report, the corresponding enterprise client, and which host node to route it to. Each host node 24 has the capability to process all incoming data from the WIRP public API 86, as well as to reject any unauthorized or invalid requests (i.e., from a host node with an invalid or expired certificate 89) as illustrated in FIG. 8.

The various client devices 26, that are owned by platform users, send data to the WIRP public API 86 that is run by WIRP Origin 60, including completed forms. The public API 86 on WIRP Origin 60 acts as a data relay for message requests by routing them to the correct host node virtual machines 82 and should not store any of the data directly, nor should it directly read any of the data as it is encrypted. Once the data is received by the correct host node 24, the sending user's identity is verified with the WIRP Origin identification directory 64, and the data in the message request payload is processed in accordance with the type of form the user submitted. Once the data is processed, it is saved in the working repository that is within the encrypted container 72 which is mounted on that host node virtual machine 82.

The Orchestrator 70 may conduct all the data management heavy work, and the host nodes 24 made by the Provisioner 80 conduct all the data processing before it is saved in the containers 72 that are managed by the Orchestrator 70. The Orchestrator 70 has no way to process the data, only to deploy, manage, and scale the containers that store the data.

In the event that a registered user wanted to send data or information to another user in the same organization or to any entity within the WIRP network 20, they would be able to do that as each user's identification is securely stored in the identification directory 64 of the WIRP Origin 60. This allows all users of the platform and the platform itself to verify and authenticate each other's existence within the network for secure communications to be established and data reports to be accessible only to those that have permission to access them. The data transfer and communication will preferably appear to be instantaneous within the platform, with exception to users with low upload and download speed.

If a device owner is trying to send an incident report to a Medical facility 56, for example a clinic, the medical facility may have its own host node created by the Provisioner 80 with a valid WIRP Certificate 66 to properly receive data from the network. WIRP Origin 60 will be able to properly relay that incident report stored and encrypted in the message request payload to that clinic's host node correctly. This allows the communication of videos, images, text, reports, and other types of data from a registered user (e.g., an employee on site) to the medical facility 56 following all the HIPAA safeguards and OSHA standards.

The Orchestrator 70 is restricted by the actual computational resources and storage capacity that it manages, so it specifies the available storage and compute capacity to a container with regards to the size of data stored in a container 72. For example, if there are twenty gigabytes of data stored in the repository of a container 72 and the Orchestrator 70 gives it twenty-five gigabytes in capacity, in the event someone uploads an incident report with an additional ten gigabytes of data, the Orchestrator 70 will receive that information and identify it as a large payload and auto scale the storage capacity of the corresponding container 72. This allows the total storage capacity of the Orchestrator 70 to be given out to containers 72 as needed.

The use of encrypted containers 72 in a data registry being managed by a container orchestration system, the Orchestrator 70, with the purpose of hosting working repositories and being mounted on remote virtual machines 82 is significant to the WIRP. The WIRP repositories are described in further detail below.

All the host nodes 24 may connect to each other depending on their need to connect, whereas all host nodes 24 need to and will connect to the WIRP Origin 60 because they utilize and require the primary services that WIRP Origin 60 renders, such as WIRP Certificate 88 issuance via the certificate authority 66, and identification verification or authentication via the ID directory 64.

If a specific data report is stored in a repository, no user without the proper permissioned access can read the data or even know it is there. Even WIRP admins only know the data capacity and payload traffic in the network 20 and/or in certain containers 72, but not what is inside the data payload or containers 72. So, permissioned access to certain data is also significant to the WIRP. The WIRP data committed to the repositories is immutable, so that changes to a parent state of a repository require committing the changes with respect to the parent state to create a child state of the repository, which allows authorized users to see a history of changes and updates made to a respective repository. Data may not be removed from a repository after it is committed, since permissioned users can see all previous saved/committed states of the repository, so long as the repository still exists. Updates change the saved state of the encrypted container, and saved container state changes are pushed to the WIRP Origin container registry 62 and backed-up as a new version of the container 72.

Each deployed and stored container 72 may have a series of tags, which can be used to identify what is generally stored in the container. Each branch of a WIRP Repository may utilize a series of tags, which allows incident data to be compartmentalized from other incidents, as well as sub-branches with sub-tags for when only a portion of the WIRP data relating to an incident should be shared with another user or user group. This allows each user to only see the data that they need to see to get their job done, as well as keep a full history of all data relating to an incident. For example, a tag may be #WIRP_ID009468_SlipAndFall-Medical or WIRP_ID009468_SlipAndFall-Insurance.

Secure communication channels use the Station-to-Station cryptographic key agreement scheme to provide user or entity authentication as well as prevent man-in-the-middle attacks. As discussed above, each host node 24 must have a valid cryptographic certificate 88 in order to communicate with other host nodes 24 in the network 20. An exception to this rule may be communication between WIRP Origin 60 and a host node 24 that does not yet possess a certificate 88 where WIRP Origin 60 acts as the certificate authority 66. If a host node 24 does not have a valid WIRP Certificate 88, they will not receive message requests from users nor be able to access any other part of the network 20 with the exception of the WIRP Origin's certificate authority 66 and the Provisioner 80, if the host node 24 was created by the Provisioner 80.

It is noted that the WIRP system 50 may also provide a stand-alone protocol for self-hosted and/or on-site Enterprise host nodes. Such a protocol may be similar to the above described approach, but Enterprise clients can operate their own host nodes with their own computational resources. These self-hosted or on-site host nodes would still communicate with WIRP Origin 60 and act just like any other host node with respect to the public API 86, however it may not have any access to the Orchestrator 70, the Provisioner 80, nor the private API 84.

Figure 9:
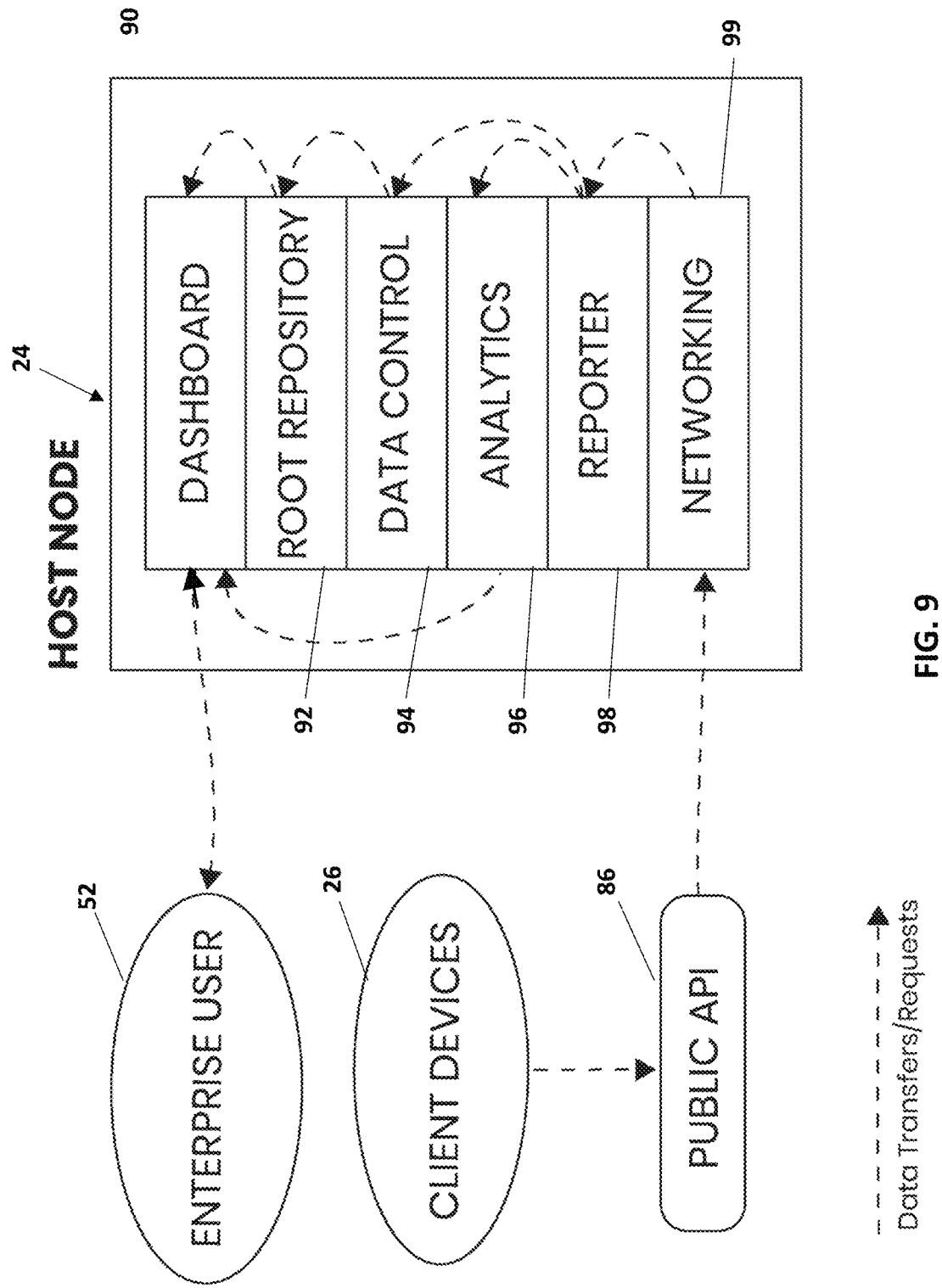
FIG. 9 is a schematic diagram illustrating WIRP service connectivity with the WIRP Origin public API and a host node in accordance with features of the present invention.
Figure 10A:
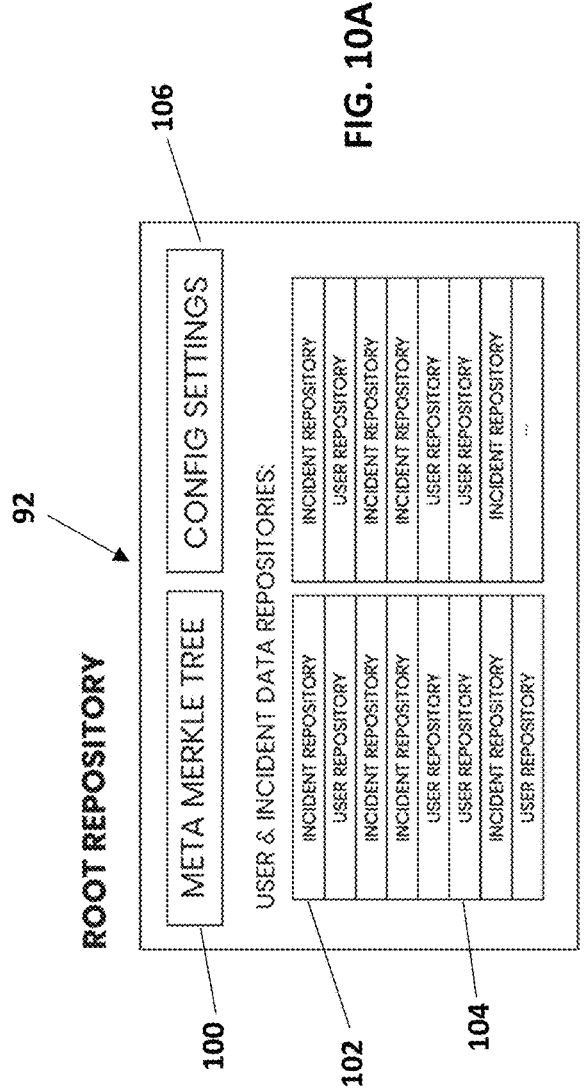
FIG. 10A is a schematic diagram illustrating an example of a root repository arrangement in accordance with features of the present invention.
Figure 10B:
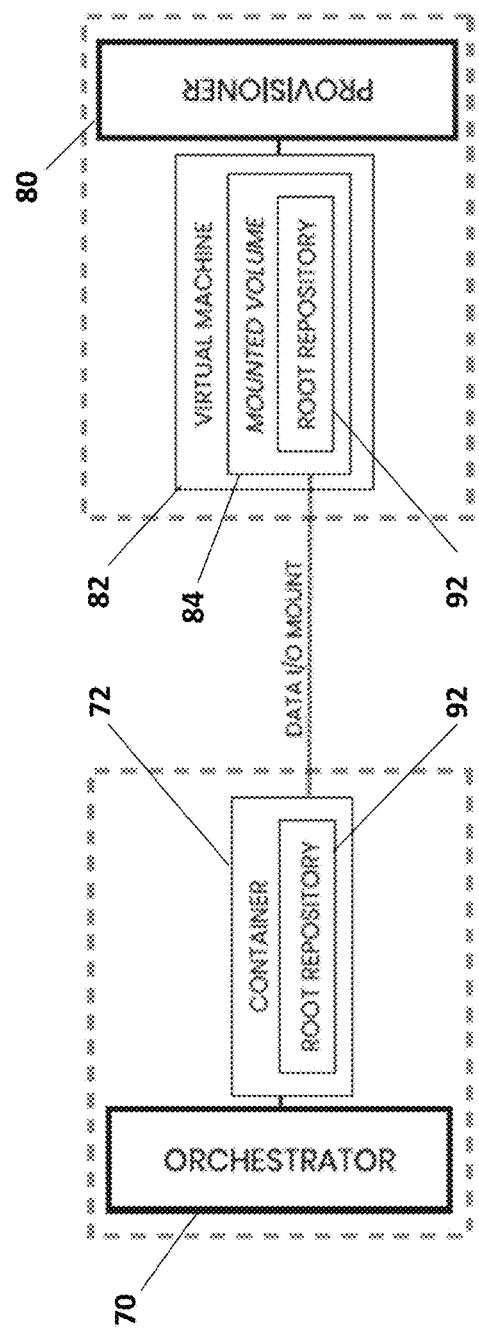
FIG. 10B is a schematic diagram illustrating an example of the root repository of a container being mounted as a mounted volume within the virtual machine of the Provisioner.

Further details of the host nodes 24 and repositories will be described below with additional reference to FIGS. 9, 10A and 10B. FIG. 9 is a schematic diagram illustrating WIRP service hierarchy and connectivity with the WIRP Origin public API 86 and a host node 24. FIG. 10A is a schematic diagram illustrating an example of a root repository arrangement, and FIG. 10B is a schematic diagram illustrating an example of the root repository 92 of a container 72 being mounted as a mounted volume 84 within the virtual machine 82 of the Provisioner 80.

Management of users on a host node 24 is controlled through a dashboard 90, analytics of workplace data may be observed through the dashboard 90, and other features of a host node 24 can be accessed through the dashboard 90. The dashboard 90 may be a user interface (UI) presented on a computer display and accessed via network connectivity, as described herein. There may be different layouts of the dashboard 90 depending on who is logged into the dashboard, where this allows for better data privacy management and permissions.

Incident Data Repositories 102 are used to manage, record, and store incident data in a container 72 mounted to the host node 24 with complete history of edits and commits to that data. User Data Repositories 104 are used to manage, record, and store user data in a container 72 mounted to the host node 24 with complete history of edits and commits to that data. Other data repositories may include analytics data repositories or educational and safety data repositories, for example.

A root repository 92 or root directory is the first or top-most directory in the hierarchy, as illustrated in FIG. 10A, and here including incident repositories 102 and user repositories 104 that are mounted from the containers 72. Each repository of user data that is listed in the root repository 92 and managed by a host node 24 will have all of the commit hashes, an indication of the user that pushed those commits, an indication of the repository the commits are in, the name of the head in that repository where the commit was made, and a timestamp recorded into the meta Merkle tree 100 or hash tree. This allows general record keeping of changes amongst the data of the whole host node 24. The contents of the commits are not recorded in this meta Merkle tree 100, only references to the data, hence the recording of the commit hashes and related information. Configuration settings 106 of the repositories may also be managed within the root repository 92. The root repository 92 within a container 72 deployed by the Orchestrator 70 is mounted as a mounted volume 84 within the virtual machine 82 provisioned by the Provisioner 80, as illustrated in FIG. 10B.

Data Control 94, or Source Control, or Version Control, includes repository data management. A branch manager manages permissions so users making changes do not have direct access to a main branch of a repository, and permissions can be set where only relevant information relating to an incident can be seen. In the analytical metrics module 96, data comes in through networking 99, and the data is duplicated where the duplicate is stripped of any personally identifying information. The original data goes to the reporter module 98 where a report (e.g. a data file or PDF report) is generated from the incident information. The data is then stored with the newly generated report in the user's repository 104.

A reporter module 98 takes in new information from client devices/applications by users, and generates reports and related assets from that data. A networking module 99 allows client software data to be received over the Internet, and for host nodes 24 to connect between other host nodes and WIRP Origin 60 in the WIRP network 20. Also, a cryptography module (not shown) may manage all of the cryptography needs used by other modules to make the WIRP system and method operate securely.

Repository Data Management includes the root repository 92 (e.g., /.wirp/commits or /user/report) which may be any empty directory assigned to be the root of the WIRP system 50 on the resources designated to become host nodes 24. Each repository may include a set of commit objects, and a set of references to commit objects referred to as heads. A use case for a repository in the WIRP system 50 is for a single individual's records, files, and data pertaining to medical and workplace incidents. In the WIRP, a repository is a directed acyclic graph of commit objects, with points in each commit object to parent commits. All pointers orient backwards in time, where eventually it links to the first commit object of a repository that has no parent.

A commit object may include: (1) a set of files, reflecting the state of a repository at a given point in time; (2) a single or multiple references to parent commit objects; and (3) a unique hash identifier that identifies the commit object, where this identifier is composed of a hash of relevant aspects of the commit, for example, so a commit with identical data with always result in the same hash identifier due to that commit not being unique. Each commit shows the changes made to a repository, and therefore represents a state change of a repository. Parent commit objects are those that were used to produce the subsequent state of the given repository. The latest commit represents the current state of a repository, while all referenced parent commits from that latest commit represent the history of that repository.

To create a commit, actions should be executed to: specify which files to include in the new commit; where if the file(s) have not changed since the previous commit that is referenced in this new commit as the parent, then the file is ignored; or if the file(s) are recognized to have changes, then those changes are recorded by individual lines in the file(s); fill in the values of the commit object data structure, where the current head will be the parent, and then this new commit object becomes the new head once committed to the repository; If a client is making the commit, they would push it to their host node.

A head is a reference to a commit object, and there can be any number of heads, with main head being the default head of a repository. HEAD in capital letters is the alias for the current head that a user is observing. The point of heads is to provide a simple abstraction of commit objects so that certain commits can be accessed easier than going backwards in commits to find the history, or for use in branching.

Branches are forks in the straight history of commits in the directed acyclic graph of a repository, from the main head or HEAD, where the history of the repository's commit objects is split where multiples heads are allowed. Each branch includes a head. The branches in the WIRP may be full repositories, which allows branches that are within a larger repository to be shared as if they were their own repository. Once a new branch is created, it has the ability to make another branch within itself, and thus another subordinate repository that could be shared by an outside user to the host node 24 without revealing information and data from the upper level repository(s).

Clients or users of a host node that are viewing data held in a repository's branches may only view one branch or employee's data at a time. The act of switching from one branch to another is generally known as a "checkout" in version control, where the client checks-out another branch to view and possibly make commits toward. What this does is change the current head the client is viewing to the one they would like to view next. The following actions may need to be executed to do so: 1) Client points their HEAD to the header alias they specify, or directly to the commit object they specify; and 2) The client's local directory of data from the host node is deleted and rewritten with all of the files stored/specified under the new HEAD commit object from the host node.

Merging is the action of finding changes between two specified branches and then combining the changes into a single branch. The following actions may be executed to do so: 1) Client or user specifies two branches, the first is the current branch they are in, and the second is the branch they wish to merge with the current branch, and in the event of uncommitted changes being made to a branch, the merge would abort; 2) A common ancestor commit object is found between the first and second branches; 3) If the ancestor commit object is equal to the commit object of the second branch, then there are no commits to merge; 4) If the ancestor commit object is equal to the commit object of the first branch, then the commit object of the first branch is set to the ancestor commit object since there are no actual changes to merge, but there are new commit objects present; 5) If neither step 3 or 4 are valid, then the changes between the ancestor commit object and the commit object of the second branch are determined, which is known as the delta; 6) Once the delta is known, then those changes are implemented into the first branch as a new commit, and in the event of conflictions during merging, the action is aborted; 7) The HEAD is set to that newly created commit; and 8) The second branch is archived, or may be deleted.

Each authenticated user or validated client to a host node 24 has specified permissions, either allowing very specific access to certain increments of data (e.g. insurance), or a whole view of multiple branches (e.g. a supervisor). These permissions are specified in the host node's configuration file 106 for validated users.

An important feature of WIRP may be that each branch is also a fully working repository subordinate to the repository above it, where branches can then be shared similar to a repository would be, but where data from above a branch is not revealed. Since branches are fully working repositories in this platform, they too can have more branches within them that are more specific in data, where these more defined branches are also a fully working repository. An example of a use case for such features would be an employee's data being stored in a branch in the repository of a host node 24, and the employer would like to share a single file with the insurance company without revealing the whole employee's set of files.

Sharing access to the root repository of a host node 24 with third parties, such as medical facilities 54 or insurance companies 58, may be considered misappropriation of permissions and would result in those third parties being able to view all of the data in the root repository, which includes all employees. This is why each branch forms its own fully working repository, that way an employer can share a single repository that has, for example, a single file, with the insurance company. The single file is a branch within a branch in the root repository for the host node 24. The setting of permissions may automatically make it so all subordinate repositories in the host node 24 are private and inaccessible to that client or user, and only specified repositories in configuration are even accessible or known to that client or user.

As discussed, each host node 24 should have a valid cryptographic certificate to communicate with other host nodes on the network 20. The WIRP system 50 identity certificate format may be, for example, a modified public key certificate (e.g., an X.509 public key certificate) with the addition of specific information pertaining to the legal entity that owns the host node, thus creating a new, derivative public key certificate standard for the WIRP system 50. The intermediate network certificate is held by WIRP Origin 60 as the certificate authority, where all end-user network certificates for host nodes 24 are digitally signed by the certificate authority 66. If a host node 24 is presenting a network certificate as a valid one representing their identity, another host node can, and should, verify the validity of that certificate with WIRP Origin 60 by checking the routing table managed by WIRP Origin 60 as well as computing a proof for the certificate authority's signature on that host node's certificate, for example.

The trust placed in WIRP Origin 60 as the certificate authority 66 is an anchor that may be generally assumed and not derived. With the addition of a permissioned distributed ledger, all host nodes 24 have a local copy of the network routing table that is synced with WIRP Origin's authority to update it. This table acts as a sort of directory for every authenticated host node 24 on the network 20, and thus can be used as a contact book when establishing communications. The structure of this routing table may be a hash table, where the contents of the table are used to generate a root hash that is then used as an identifier for the state of the table at any time. Each change or update in the contents of the table results in a new state change and an incremental increase in a counter, for example.

Any host node 24 on the network 20 can have any other host node's information stored in this routing table, with no minimum or maximum amount of contacts required to be stored, for example. The full listings, contents, and history of the routing table should be maintained by WIRP Origin 60, where any host node 24 on the network 20 may request such information from WIRP Origin 60. To derive trust cryptographically regarding the history of a ledger, for example, WIRP Origin 60 may need to maintain the full list of changes and updates to the ledger in increments of sixty second blocks of both time and data, for example. In these blocks, only changes to the state of the ledger may be recorded, and not the actual whole state of the ledger during that block. Each new block makes a reference to the previous block that came before it, known as a parent block. This structure may form a blockchain that allows for any permissioned peer on the network 20 to see the full history of changes from the inception to the current state of the ledger. With such a system in place, both assumed and derived trust can be placed in WIRP Origin 60 as the certificate authority 66.

For secure communication channels, the WIRP may implement a Station-to-Station protocol using, for example, X25519 keys for Diffie-Hellman key-exchange and ChaCha20/Poly1305 for encryption. Use of ChaCha20/Poly1305 has been standardized by the Internet Engineering Task Force in RFC 7905. Of course, other encryption techniques may also be appropriate. So, the WIRP may preferably implement the Station-to-Station protocol using: X25519 keys for Diffie-Hellman key-exchange; ChaCha20/Poly1305 for encryption and stream cipher; HMAC-SHA256 as MAC; and HKDF for key derivation.

For encrypted messaging, each client and host node initially generate an identity public-private key-pair (from Curve25519 as an example), and a set of pre-keys. During host node 24 registration with WIRP Origin 60, that host node would upload their pre-keys to be bundled with their public key, and this information is included in the signed network certificate that the host node 24 would receive from WIRP Origin 60. The pre-keys and public key of a host node 24 can be used by another host node to derive an initial encryption key even if the receiving host node is offline at the time, and then asynchronously initiate an encrypted stream to have communication or conversation. Using the station-to-station protocol and certificate authentication will ensure that no "man-in-the-middle" attacks can take place.

For a client to send encrypted data to their host node, they must have a cryptographic session established, where the cryptographic identity and fingerprint of the client is pre-recorded on the host node 24 and thus can be viewed and compared before the cryptographic session is established. This will also prevent "man-in-the-middle" attacks between clients 26 and host nodes 24, since both the client and the host node have verified their ID over the network 20.

Figure 11:
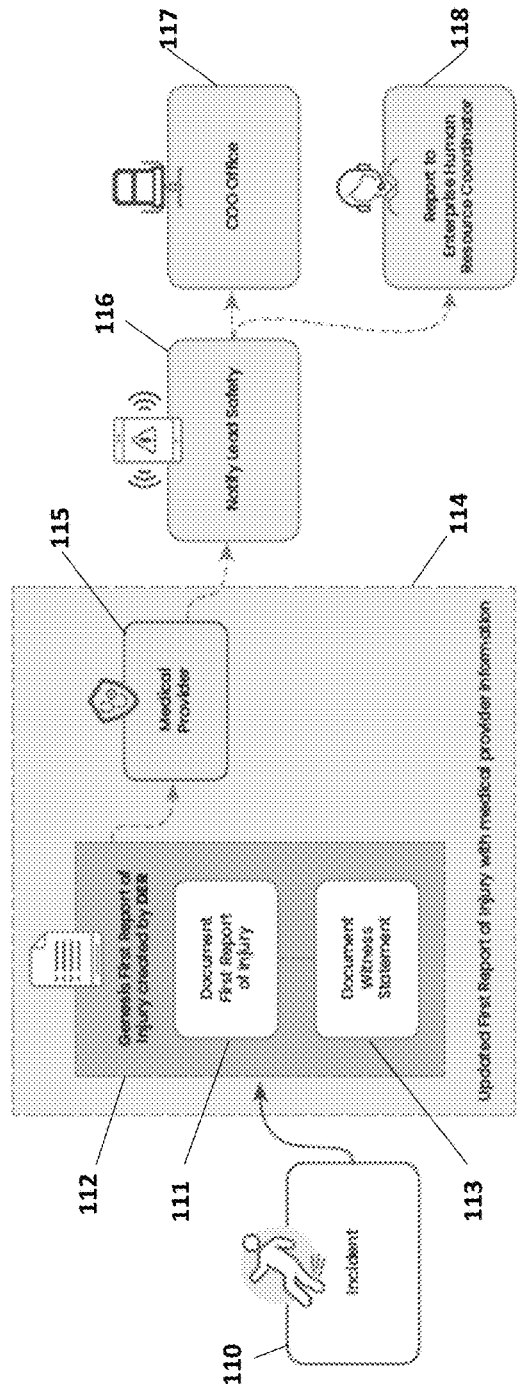
FIG. 11 is a schematic diagram illustrating an example of the internal flow of incident reporting for a WIRP Enterprise in accordance with features of the present invention.

FIG. 11 is a schematic diagram illustrating an example of the internal flow of incident reporting for a WIRP Enterprise client 52. The diagram in FIG. 11 represents the enterprise client company flow of WIRP information data internally starting, within the employee's company, beginning with a new incident 110. The DER creates a First Report of Injury (FRI) 111, also known as the genesis data block 112 starting the WIRP data compilation process. All remaining data in this process may be built on (additions to) the FRI report 111. In the genesis first report 112, the DER inputs injury or incident data, pulls real-time coordinates information, weather report, adds images, text, videos, or voice recordings, along with a witness statement 113. The witness statement 113 may be added at a later date as an attachment to the incident report. The injured employee/associate statement may also be added depending on availability and safety. All the information may define the WIRP incident file 114.

Next, specific preauthorized information, requests and reports are sent to the medical provider 115, and the DER and medical provider's databases sync with updates. Once the medical provider 115 (e.g., emergency or urgent care provider) updates the WIRP incident file 114, the lead safety 116 or DER will receive updated information that is automatically processed to controlled reports for the management or company leadership 117 and human resources coordinator 118 to process worker compensation and other administrative tasks. The WIRP incident file 114 will remain open and update until the file is declared completed or closed by the DER or HR, then it is archived.

Figure 12:
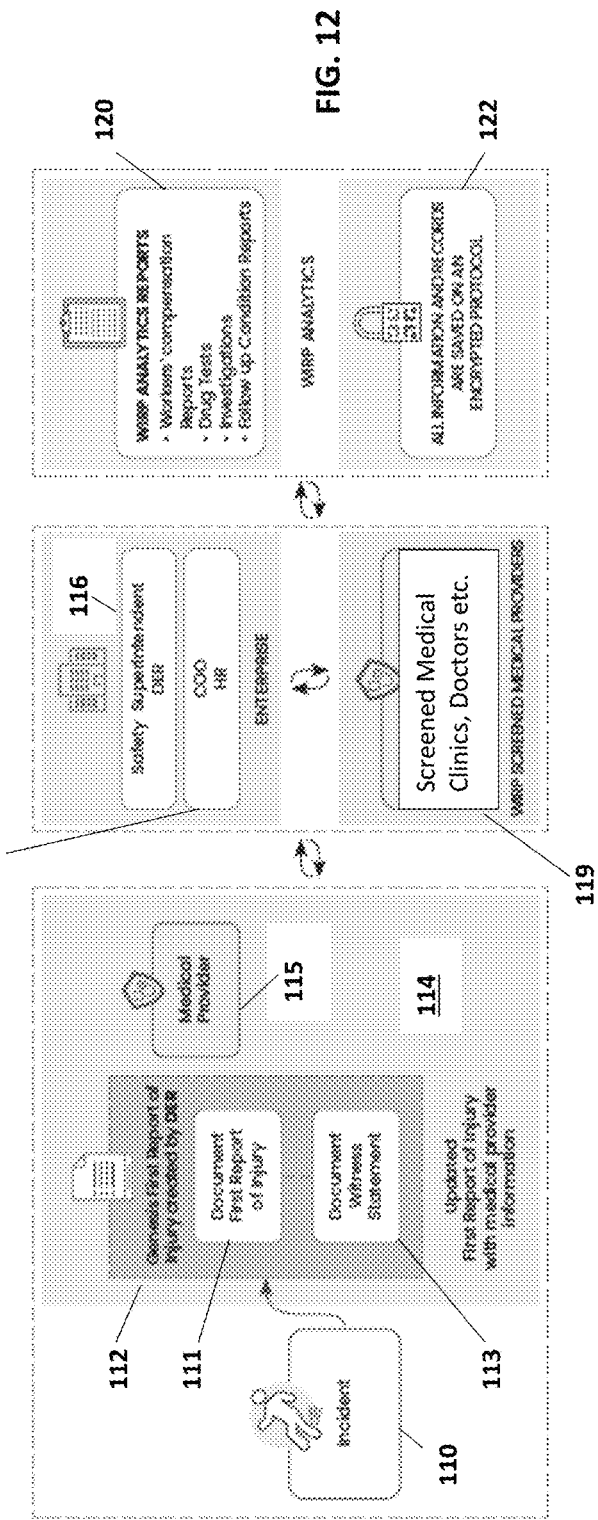
FIG. 12 is a schematic diagram illustrating an example of the external flow of incident reporting for a WIRP Enterprise in accordance with features of the present invention.

FIG. 12 is a schematic diagram illustrating an example of the external flow of incident reporting for a WIRP Enterprise client 52. All the internal information as illustrated in FIG. 11 is processed and flows in a controlled manner between the WIRP enterprise client 52, medical provider 115, lead safety 116, company leadership 117 and human resources coordinator 118. Screened Medical Providers 119 (e.g., non-emergency Clinics, Doctors etc.) who treat the associate may receive requests and provide medical status updates to the WIRP incident file 114. Subsequently, WIRP data of incident information (e.g., HIPAA compliant, private or controlled) is processed by WRIP analytics reports 120 (e.g., workers comp, drug test, investigations, follow-up condition) and the WIRP data becomes secure WIRP records 122 and are saved within the WIRP system 50 using the encryption approaches discussed above.

Figure 13A:
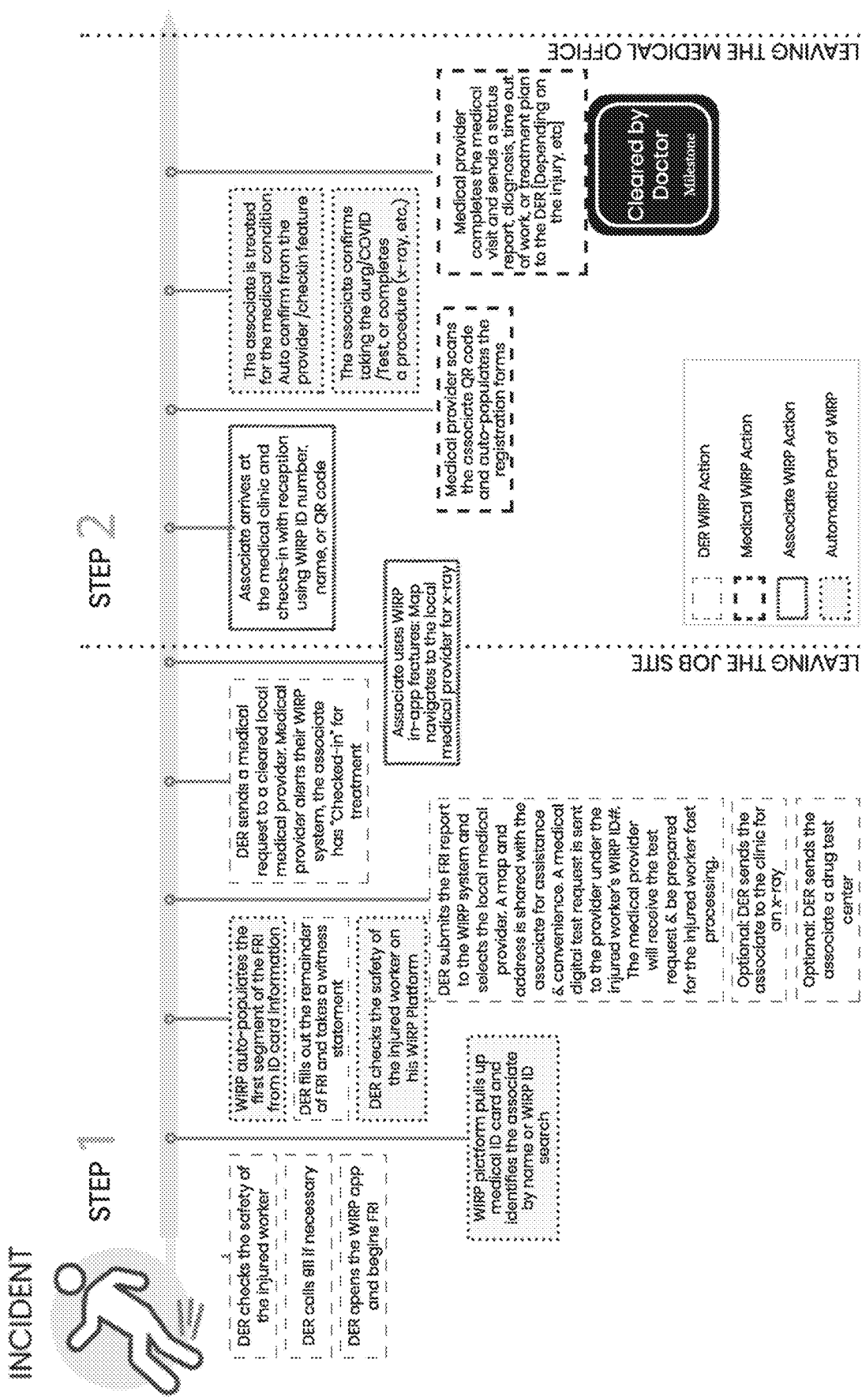
FIGS. 13A and 13B are schematic diagrams illustrating an example of the journey of incident reporting for a WIRP Associate user in accordance with features of the present invention.
Figure 13B:
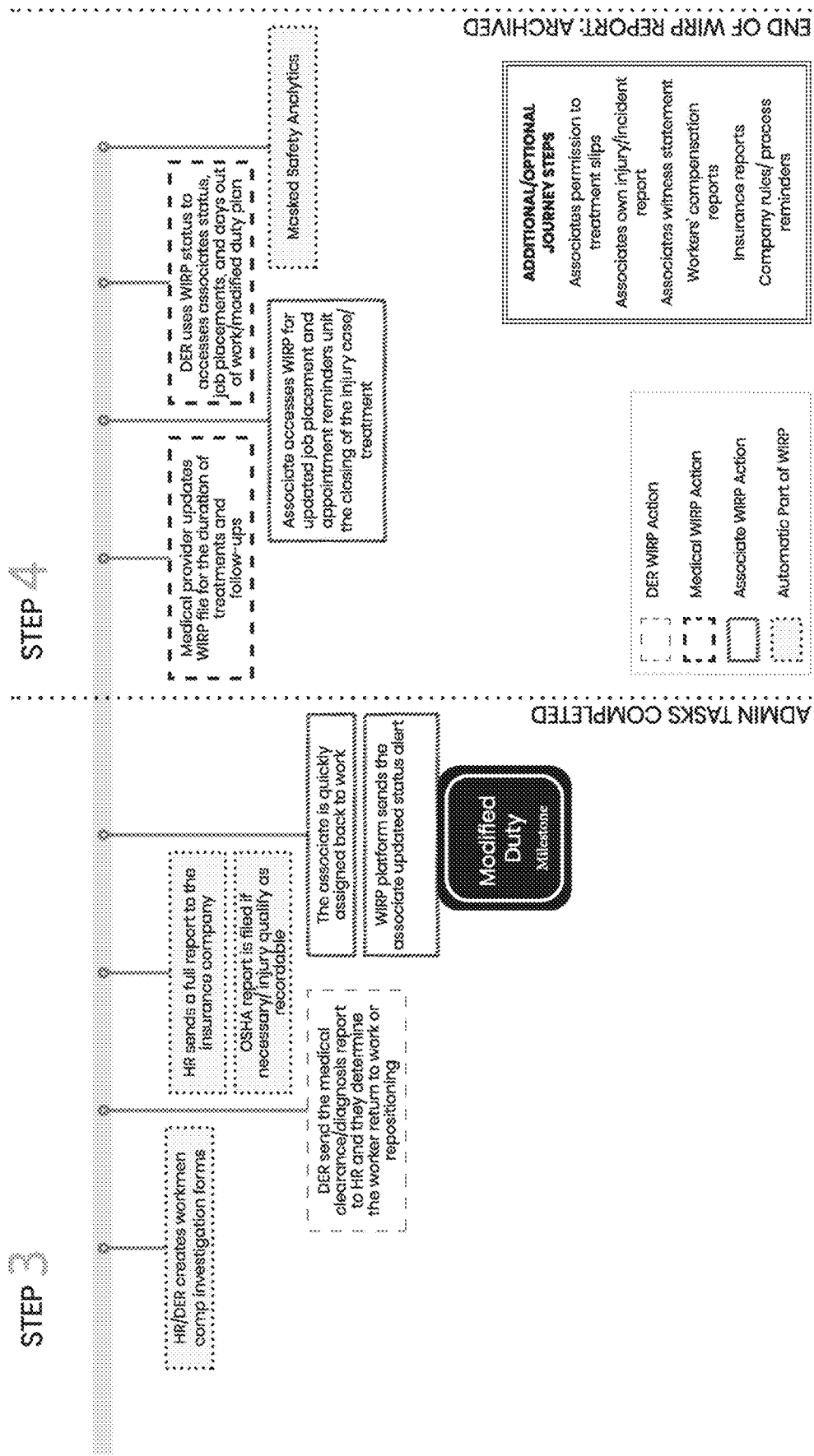
Figure 14D:
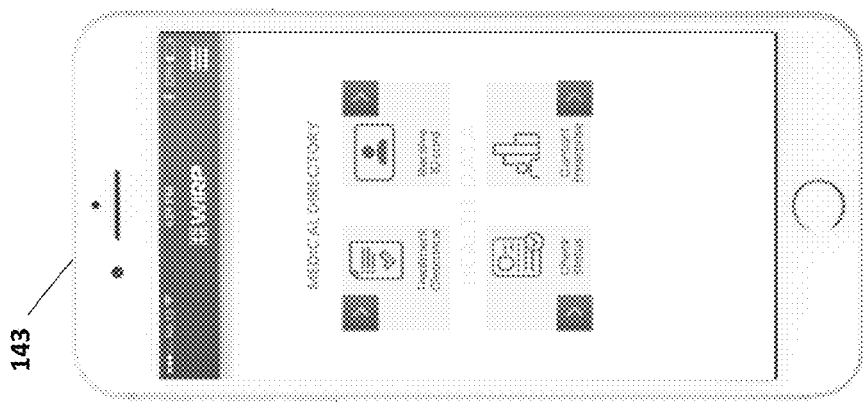
FIGS. 14A-14D are schematic screenshots illustrating examples of the mobile application user interface for incident reporting within the WIRP in accordance with features of the present invention.
Figure 14C:
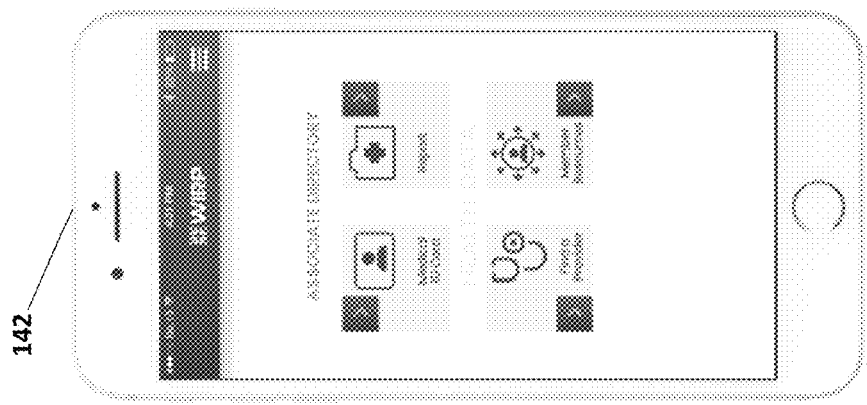
Figure 14B:
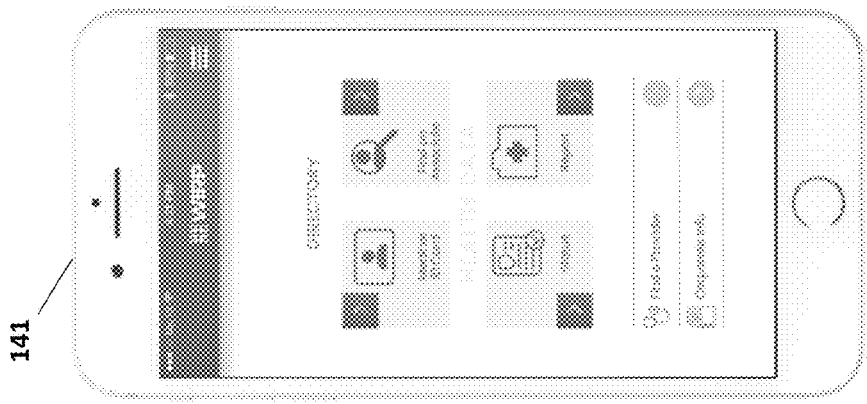
Figure 14A:
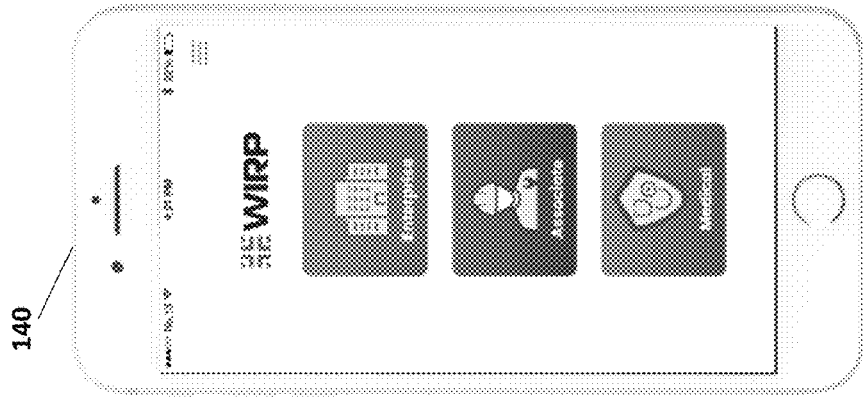

An example embodiment of the journey through the WIRP approach will now be described with reference to FIGS. 13A and 13B. It begins with the First Report of Incident (FRI). Under STEP 1, the DER checks the safety of the injured worker, and calls emergency services (e.g., 911) if necessary. The DER opens the WIRP app and begins the FRI. The WIRP system 50 pulls up medical ID card and identifies the associate by name or WIRP ID search. WIRP auto-populates the first segment of the FRI from ID card information. The DER fills out the remainder of FRI and takes a witness statement. The DER checks the safety of the injured worker. The DER submits the FRI report to the WIRP system and selects the local medical provider. A map and address may be shared with the associate for assistance and convenience. A medical digital test request is sent to the provider under the injured worker's WIRP ID. The medical provider will receive the test request and be prepared for the injured worker with more efficient and faster processing.

Optional steps include: the DER sends the associate to the clinic for an X-Ray or to a drug test center.

Then, the DER sends a medical request to a cleared local medical provider. The medical provider alerts the WIRP system 50 that the associate has digitally "checked-in" the system for treatment.

Leaving the job site, beginning STEP 2, the associate uses WIRP in-app features such as the Map which navigates to the local medical provider for x-ray/treatment. The associate arrives at the medical clinic and physically checks-in with reception using WIRP ID number, name, or QR code. The medical provider scans the associate QR code and auto-populates the registration forms. The associate is treated for the medical condition. For example, the associate takes the drug test, or completes an x-ray, etc. The medical provider completes the medical visit and sends a status report, diagnosis, time out of work, or treatment plan to the DER (Depending on the injury, etc.). The associate may be cleared by the doctor.

Leaving the medical office, STEP 3, HR/DER creates workers comp investigation forms. The DER sends the medical clearance/diagnosis report to HR and they determine the worker return to work or repositioning. HR sends a full report to the insurance company. An OSHA report may be filed if necessary, i.e., the injury or illness qualifies as recordable. The associate may be quickly assigned back to work. The WIRP system 50 sends the associate updated status alert, for example, "Modified Duty."

Admin tasks completed, STEP 4, the medical provider updates the WIRP file for the duration of treatments and follow-ups. The associate accesses the WIRP for updated job placement and appointment reminders unit the closing of the injury case/treatment. The DER uses the WIRP status to access associates' status, job placements, and days out of work/modified duty plan. Masked safety analytics may be generated.

Additional/optional journey steps may include the issuance of an associate's permission to treatment, an associate's own injury/incident report, an associate's witness statement, workers' compensation reports, Insurance reports, and company rules/process reminders.

Referring additionally to FIGS. 14-19, examples of various features in the WIRP mobile and web platforms will be described. To better understand the usability of the WIRP, a customized interface may be developed for various user categories. For example, mobile device app user groups may include the Designated Employee Representative (DER) who is the point person within each enterprise who is responsible for creating/managing First Reports of Injury (FRI). Examples include a Foreman, Safety Officer, Superintendent, or Project Manager. Medical Providers may include all local and regional healthcare providers who work with WIRP industry clients. Examples include local screened clinics, local screened doctors, onsite clinics, emergency rooms or labs.

Additionally, web platform user groups may include Enterprise Leadership who are business leaders that will use the WIRP's reports to build safety strategies and manage employee and contractors. Also, Human Resources (HR) will benefit from the WIRP's detailed and comprehensive reports that will streamline employee positioning placement and management. Insurance Companies, such as business health insurance companies, individuals and co-op insurance groups, reinsurance companies, and/or insurance claim investigators.

For example, FIGS. 14A-14D are schematic screenshots illustrating examples of the mobile application user interface (UI) for incident reporting within the WIRP. A user will select a user group type upon downloading and opening the app for setup. A main directory 140 is shown and includes selection icons or buttons (graphical control element or dialog box), for example, for the Enterprise, the Associate and the Medical Provider. Selecting the Enterprise box will bring the user to an Enterprise Directory 141 which may provide selectable search access and data entry boxes such as Medical ID Card, Find an Associate, Status, and Report to access various WIRP features described herein. Find a Provider and Corporate information selection boxes may also be provided. Selecting the Associate box will bring the user to an Associate Directory 142 which may provide selectable search access and data entry boxes such as Medical ID Card, Find a Provider, Member Resources, and Report to access various WIRP features described herein. Selecting the Medical box will bring the user to an Medical Directory 143 which may provide selectable search access and data entry boxes such as Treatment Clearance, Receive ID Card, Check Status, Contact Enterprise to access various WIRP features described herein. The Medical providers' segment may have customizable features based on the location, type of practice, drug screening, COVID test, and any post-incident test. This segment connects/syncs to the Enterprise and Individual user interface based on the type of information requested.

The features provided on the WIRP to the various users may include: Mobile & Device Support for iPhone (105), Android, and Web, for example; Data Analytics including scalable database FRI forms, and scalable database witness statements; and auto fill worker ID information. The registration verification tools may require: validation of both an email address and phone number to get started; employer invite code/tokens; registration security including two factor authentication, and One-Time-Password (OTP) or Authenticator application; and a WIRP ID verification tool. A Profile Builder may include: Assigning WIRP ID at sign up; Verifying email address and phone number; Verifying Authenticator; Profile status indicator; and Scheduling tools such as calendar integration, and alerts and appointment reminders. Other features are contemplated.

Other features may include Incident Report Creation with: Filling out report forms; Depositing forms as a pdf; Date and time stamping; Weather conditions API integration; Geolocation maps may pinpoint incident location; Multimedia (photo and video) capturing of incident; Annotation of photographs; Auto fill ID cards based on WIRP # or Name; In-app messaging; and Bio-med features via health apps such as Apple Health Kit or Google Fit, for example. Indicator features may include: Search for associates in enterprise database and/or Pull 'snapshot' of employee records; Pull status record 'snapshot' of associates past reports, the snapshot shows year of incident, status resolved, status open, report criticality level indicated by icon color, for example; Time out of work tracker and indicator; Return to work status indicator; Short summary of report status (in treatment, in recovery, on leave, return to work, unable to return to work, etc.); and Notification badges.

Additional features are discussed below. Quality control includes Quick surveys and Information security, such as: Password reset token; Encrypted communication channels between host nodes [WIRP ID] as a unique identifier for platform users, and between client users [mobile app]; Concealing key sensitive data (###); and biometric security such as FaceID and TouchID, for example, as password abstractions. Realtime features include Maps: Geo status sharing; Navigations; and Finding local screened medical providers. Weather Reporting includes a Date & time stamp. An Auto Check-in feature, based upon a geofence, for example may be included.

Integrated analytics features include: Analytics pull; Local defined; Analytics data concealing; WIRP annotated analytics; Auto updates; Smart analytic systems with search features; Report streamlining; and the Integration of descriptive analytics, diagnostics analytics including segmentation and filters, predictive analytics, and prescriptive analytics. Type of reports include: First Report of Injury; Incident report zero to sixty with company specs; Witness Statements; Insurance reports; Safety reports; and Internal enterprise reports, for example.

Figure 15:
FIG. 15 are examples of user interfaces for the mobile application and web application for the WIRP on various computer devices in accordance with features of the present invention.

FIG. 15 illustrates examples of user interfaces for the mobile application and web application for the WIRP on various computer devices including mobile phones 150, tablets 152, desktops 154 and laptops 156, for example.

Figure 16:
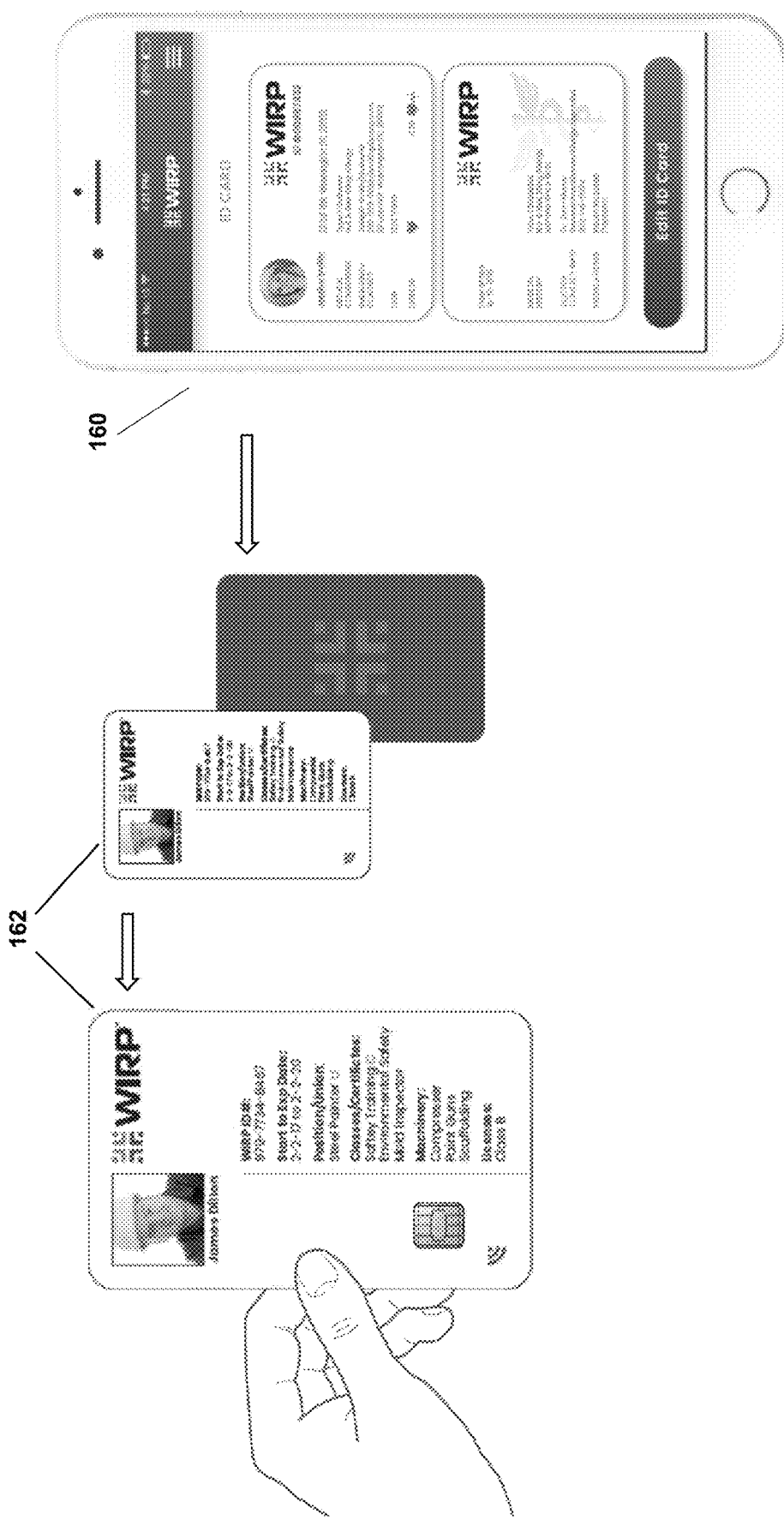
FIG. 16 is a schematic diagram illustrating an example of the digital and physical employee ID card for WIRP in accordance with features of the present invention.

FIG. 16 is a schematic diagram illustrating an example of the Identification card which may include a digital ID 160 and physical employee ID card 162 for the WIRP. The front end for the associate/individual user interface may have several key features that can customized to each person and to each report type with unique feature sets. Features may include a digital medical ID card 160 to identify a WIRP ID number (Public key), basic vital information e.g. blood type, organ donor status, and insurance phone number, emergency contact, any medical conditions that are voluntarily listed by the user e.g. Diabetes, food allergies, etc. The ID card 160 may be customizable by each individual user. The Individual user profiles can be used independently or connected to any enterprise system of choice. A private log of incident reports may be stored locally on each individual device with options to share or archive certain data. A log of each filed and submitted witness statement may also be available on the private log. A wellness portal may be customizable based on the industry, interest, and/or job title of each user. The wellness portal will host useful information such as extended learning, safety training, wellness tidbits and information, industry influencer videos, etc.

The associate platform will sync with a one-time assigned WIRP ID that stays with the individual digitally 160, locally and private on their mobile device, and optionally operates on both local and centralized systems. The WIRP ID may also include a physical hard ID card 162, for example, with printed information, and/or smart card (contactless card) protected storage and access capabilities such as near field communication (NFC), etc.

Figure 17C:
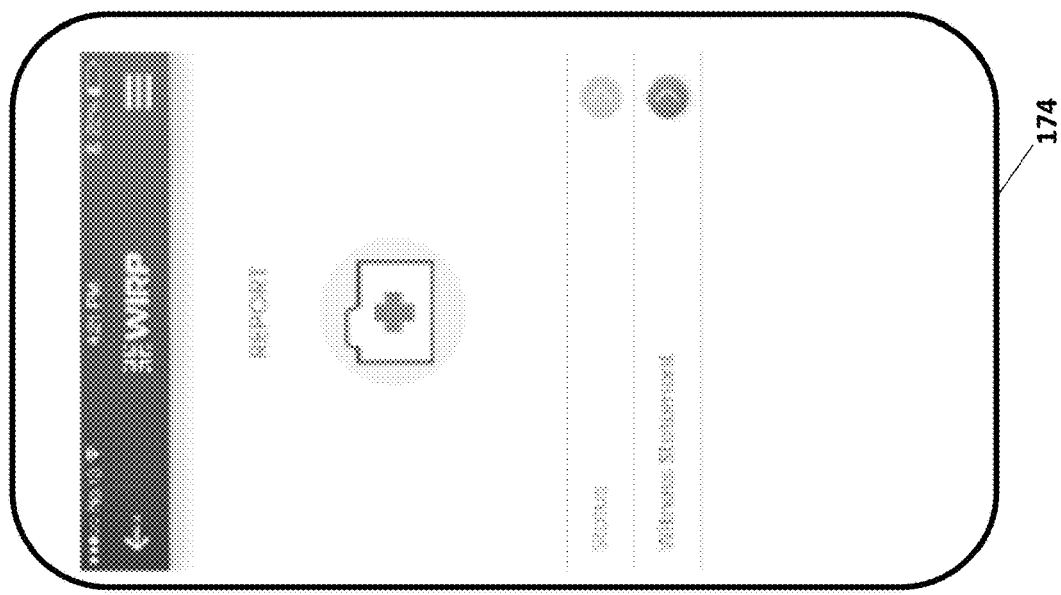
FIGS. 17A-17C are schematic screenshots illustrating examples of the mobile application user interface for incident reporting within the WIRP in accordance with features of the present invention.
Figure 17B:
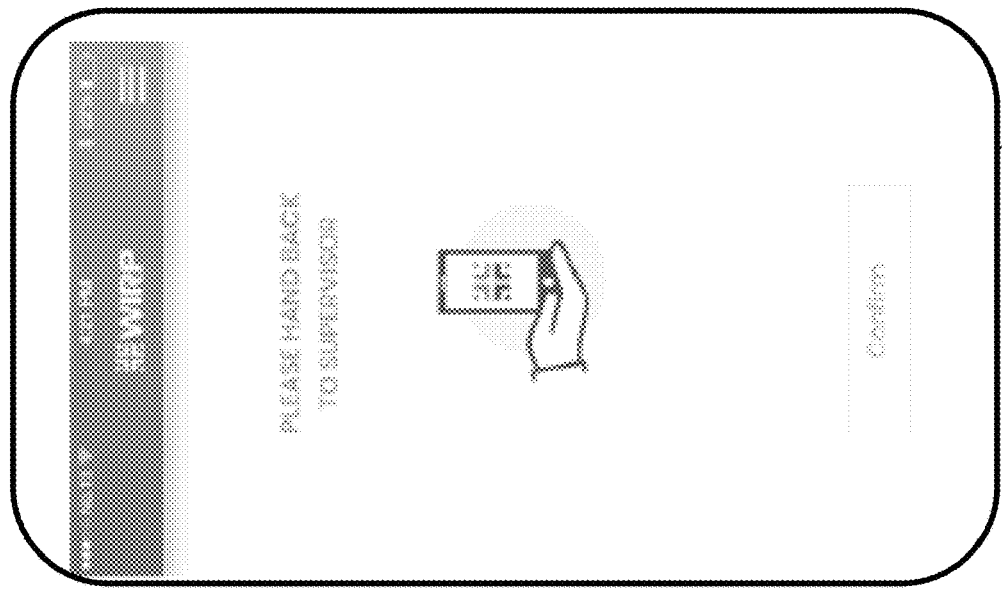
Figure 17A:
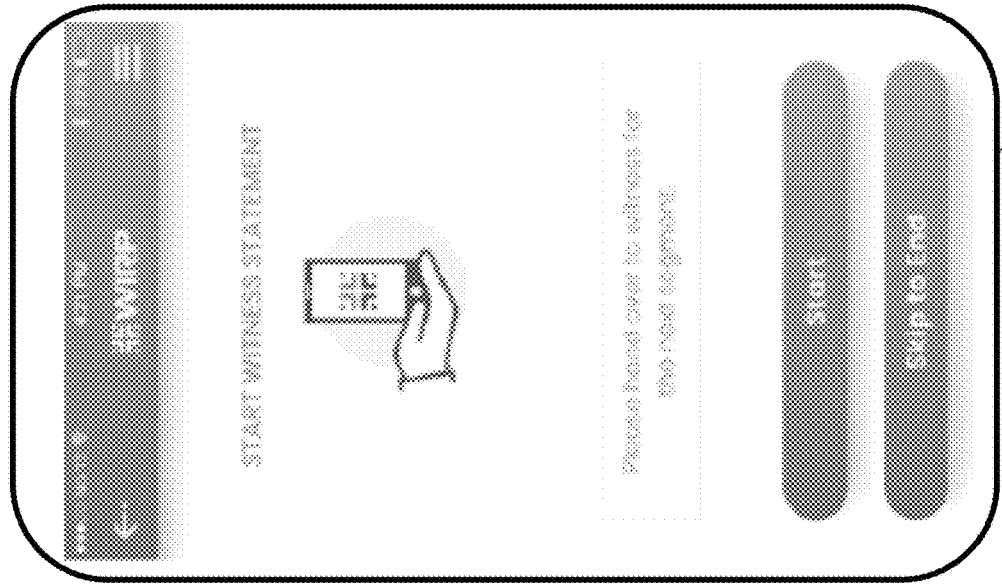

FIGS. 17A-17C are schematic screenshots illustrating examples of the mobile application user interface for incident reporting within the WIRP. Users have the capability to provide a Witness Statement via their own mobile device with the WIRP application installed, or they may create a witness statement using an Enterprise device (e.g., the DER's device). As illustrated, the Witness Statement access box 170 includes various options and instructions, such as, to "hand over to witness for the next segment". A form may then be completed by the witness immediately after the incident or even at a later date. After submission, the form data is processed as WIRP data in the WIRP system 50, as described above. The witness may then be instructed to give the device back to the Supervisor as illustrated in the screenshot 172 of the UI. A UI screen 174 may then provide options for viewing the Status report or the Witness Statement reports.

FIG. 18 is a schematic screenshot 180 illustrating an example of the mobile application user interface including a body map 182 for incident reporting within the WIRP. A user may select from a drop-down menu 184 or actually touch the body map (via touch screen enable device) to indicate any injuries or pain being experienced by themselves and/or for an injured employee.

FIGS. 19A and 19B are schematic screenshots 190 and 196 illustrating an example of the mobile application user interface including geolocation maps 191 and 197 for incident reporting and/or provider location within the WIRP. Images 192 and videos 193 submitted within the FRI and/or as incident statement forms may include geo-location tags that display on the map 191. Finding a Medical Provider may be a feature that includes a list or display map 197 of facilities based upon distance and/or specialties. Options may include notifications or alerts being sent to the Associate and/or to the Medical Facility.

Value in the WIRP includes Socioeconomic, Economic, and Technology. Socioeconomic: In the current competitive business markets, where successful companies need to build and retain talent, it is no longer good enough to only be a source for an associates paycheck. Companies need to build an internal reputation and define company culture by strategically positioning themselves as a secure and safe place to work. Collaborative resources that people can take home, including more than one use case (such as training videos, ID cards, health, and wellness portals) is exactly the type of application widely used in today's growing market for productivity applications. WIRP will enable the enterprise, medical provider, and associate to both save money and time.

Economic: WIRP will create value for the business by securing a position within each company as a go-to secure resource for risk mitigation and fraud prevention. It is a time-saving vehicle for accurate documentation, safety analytics, and in-app collaboration resources.

Technology: The digital dependency of people today (especially on mobile apps) is a catalyst to innovate disruptive technology that is spreading across the world. People expect technology to complete, not overwhelm processes, which is why WIRP utilizes user-generated ID features. Some of the major game-changing global trends growing at a rapid pace across every industry, specifically the insurance and medical industries, are based on the Hyperledger brand technology. Not only is WIRP placing the FRI process in the digital space, but the system's protocol may also operate on a distributed authentication ledger, which is an underlying technology of all Hyperledger and/or blockchain tech projects. Centralized data processing and storage is also contemplated, as well as hybrid system and method including both centralized and decentralized approaches that are customized as needed.

Systems and Methods

Figure 20:
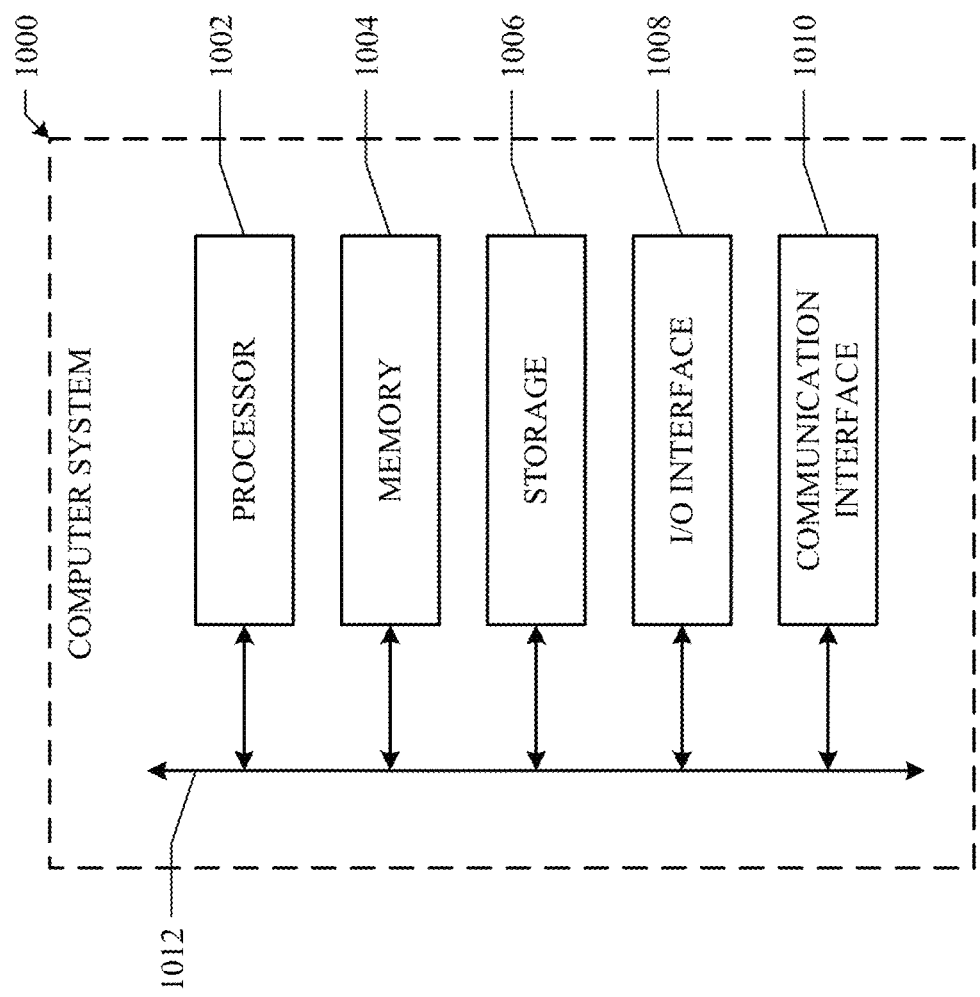
FIG. 20 is a schematic diagram illustrating a computer environment in which various embodiments can be implemented.

FIG. 20 illustrates an example computer system 1000. In particular embodiments, one or more computer systems 1000 perform one or more steps of one or more methods described or illustrated herein. In particular embodiments, one or more computer systems 1000 provide functionality described or illustrated herein. In particular embodiments, software running on one or more computer systems 1000 performs one or more steps of one or more methods described or illustrated herein or provides functionality described or illustrated herein. Particular embodiments include one or more portions of one or more computer systems 1000. Herein, reference to a computer system may encompass a computing device, and vice versa, where appropriate. Moreover, reference to a computer system may encompass one or more computer systems, where appropriate.

This disclosure contemplates any suitable number of computer systems 1000. This disclosure contemplates computer system 1000 taking any suitable physical form. As example and not by way of limitation, computer system 1000 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 1000 may include one or more computer systems 1000; be unitary or distributed; span multiple locations; span multiple machines; span multiple data centers; or reside in a cloud, which may include one or more cloud components in one or more networks. Where appropriate, one or more computer systems 1000 may perform without substantial spatial or temporal limitation one or more steps of one or more methods described or illustrated herein. As an example, and not by way of limitation, one or more computer systems 1000 may perform in real time or in batch mode one or more steps of one or more methods described or illustrated herein. One or more computer systems 1000 may perform at different times or at different locations one or more steps of one or more methods described or illustrated herein, where appropriate.

In particular embodiments, computer system 1000 includes a processor 1002, memory 1004, storage 1006, an input/output (I/O) interface 1008, a communication interface 1010, and a bus 1012. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1002 includes hardware for executing instructions, such as those making up a computer program. As an example, and not by way of limitation, to execute instructions, processor 1002 may retrieve (or fetch) the instructions from an internal register, an internal cache, memory 1004, or storage 1006; decode and execute them; and then write one or more results to an internal register, an internal cache, memory 1004, or storage 1006. In particular embodiments, processor 1002 may include one or more internal caches for data, instructions, or addresses. This disclosure contemplates processor 1002 including any suitable number of any suitable internal caches, where appropriate. As an example, and not by way of limitation, processor 1002 may include one or more instruction caches, one or more data caches, and one or more translation lookaside buffers (TLBs). Instructions in the instruction caches may be copies of instructions in memory 1004 or storage 1006, and the instruction caches may speed up retrieval of those instructions by processor 1002. Data in the data caches may be copies of data in memory 1004 or storage 1006 for instructions executing at processor 1002 to operate on; the results of previous instructions executed at processor 1002 for access by subsequent instructions executing at processor 1002 or for writing to memory 1004 or storage 1006; or other suitable data. The data caches may speed up read or write operations by processor 1002. The TLBs may speed up virtual-address translation for processor 1002. In particular embodiments, processor 1002 may include one or more internal registers for data, instructions, or addresses. This disclosure contemplates processor 1002 including any suitable number of any suitable internal registers, where appropriate. Where appropriate, processor 1002 may include one or more arithmetic logic units (ALUs); be a multi-core processor; or include one or more processors 1002. Although this disclosure describes and illustrates a particular processor, this disclosure contemplates any suitable processor.

In particular embodiments, memory 1004 includes main memory for storing instructions for processor 1002 to execute or data for processor 1002 to operate on. As an example, and not by way of limitation, computer system 1000 may load instructions from storage 1006 or another source (such as, for example, another computer system 1000) to memory 1004. Processor 1002 may then load the instructions from memory 1004 to an internal register or internal cache. To execute the instructions, processor 1002 may retrieve the instructions from the internal register or internal cache and decode them. During or after execution of the instructions, processor 1002 may write one or more results (which may be intermediate or final results) to the internal register or internal cache. Processor 1002 may then write one or more of those results to memory 1004. In particular embodiments, processor 1002 executes only instructions in one or more internal registers or internal caches or in memory 1004 (as opposed to storage 1006 or elsewhere) and operates only on data in one or more internal registers or internal caches or in memory 1004 (as opposed to storage 1006 or elsewhere). One or more memory buses (which may each include an address bus and a data bus) may couple processor 1002 to memory 1004. Bus 1012 may include one or more memory buses, as described below. In particular embodiments, one or more memory management units (MMUs) reside between processor 1002 and memory 1004 and facilitate accesses to memory 1004 requested by processor 1002. In particular embodiments, memory 1004 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1004 may include one or more memories 1004, where appropriate. Although this disclosure describes and illustrates particular memory, this disclosure contemplates any suitable memory.

In particular embodiments, storage 1006 includes mass storage for data or instructions. As an example, and not by way of limitation, storage 1006 may include a hard disk drive (HDD), a floppy disk drive, flash memory, an optical disc, a magneto-optical disc, magnetic tape, or a Universal Serial Bus (USB) drive or a combination of two or more of these. Storage 1006 may include removable or non-removable (or fixed) media, where appropriate. Storage 1006 may be internal or external to computer system 1000, where appropriate. In particular embodiments, storage 1006 is non-volatile, solid-state memory. In particular embodiments, storage 1006 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1006 taking any suitable physical form. Storage 1006 may include one or more storage control units facilitating communication between processor 1002 and storage 1006, where appropriate. Where appropriate, storage 1006 may include one or more storages 1006. Although this disclosure describes and illustrates particular storage, this disclosure contemplates any suitable storage.

In particular embodiments, I/O interface 1008 includes hardware, software, or both, providing one or more interfaces for communication between computer system 1000 and one or more I/O devices. Computer system 1000 may include one or more of these I/O devices, where appropriate. One or more of these I/O devices may enable communication between a person and computer system 1000. As an example, and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1008 for them. Where appropriate, I/O interface 1008 may include one or more device or software drivers enabling processor 1002 to drive one or more of these I/O devices. I/O interface 1008 may include one or more I/O interfaces 1008, where appropriate. Although this disclosure describes and illustrates a particular I/O interface, this disclosure contemplates any suitable I/O interface.

In particular embodiments, communication interface 1010 includes hardware, software, or both providing one or more interfaces for communication (such as, for example, packet-based communication) between computer system 1000 and one or more other computer systems 1000 or one or more networks. As an example, and not by way of limitation, communication interface 1010 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1010 for it. As an example, and not by way of limitation, computer system 1000 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1000 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1000 may include any suitable communication interface 1010 for any of these networks, where appropriate. Communication interface 1010 may include one or more communication interfaces 1010, where appropriate. Although this disclosure describes and illustrates a particular communication interface, this disclosure contemplates any suitable communication interface.

In particular embodiments, bus 1012 includes hardware, software, or both coupling components of computer system 1000 to each other. As an example and not by way of limitation, bus 1012 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1012 may include one or more buses 1012, where appropriate. Although this disclosure describes and illustrates a particular bus, this disclosure contemplates any suitable bus or interconnect.

A computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

A communication network operates in accordance with embodiments of the present disclosure. In particular, a data server communicates with client devices such as mobile terminal and personal computer via network. The network can include a single network or a plurality of different networks. These network(s) can include the Internet, a private communication network, a local area network, a mobile wireless communication network, a wired or fiber optic network or other broadband communication network.

The data server can present a website that operates via a browser application of mobile terminal and/or personal computer or that otherwise provides a server application that operates in conjunction with a client device having an application such as a mobile application selected for download by the user and downloaded to the client device to present and gather data that includes user data and preferences, and other data.

A processing module can be implemented via a single processing device or a plurality of processing devices. Such processing devices can include a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in a memory, such as memory. The memory can include a hard disc drive or other disc drive, read-only memory, random access memory, volatile memory, non-volatile memory, static memory, dynamic memory, flash memory, cache memory, and/or any device that stores digital information. Note that when a processing device implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. While a particular bus architecture is presented that includes a single bus, other architectures are possible including additional data buses and/or direct connectivity between one or more elements.

At least one processor of the processing module executes the data server application to bidirectionally communicate data with a user of a client device, such as client device via the network interface and the network.

A client device, such as mobile terminal, personal computer or other client device such as a personal digital assistant, e-reader, tablet, or smartphone is presented. The client device includes a network interface having one or more interfaces that include wireless interfaces such as a 3G, 4G or other wireless telephony transceiver, a Bluetooth transceiver, a WiFi transceiver, UltraWideBand transceiver, WIMAX transceiver, Zig Bee transceiver or other wireless interface. Examples of interfaces further include wired interfaces such as a Universal Serial Bus (USB) interface, an IEEE 1394 Firewire interface, an Ethernet interface or other network card or modem for communicating with data server, or other servers such as content servers via the network. The client device also includes a user interface such as a display device, touch screen, key pad, touch pad, thumb wheel, one or more buttons, a speaker, a microphone, an accelerometer, gyroscope or other motion or position sensor, or other interface devices that provide information to a user of the client device and that generate data in response to the user's interaction with the client device. In addition, the client device includes an image capture device such as a digital camera that captures still or video images with or without associated audio.

The client device also includes a processing module and memory module that stores an operating system such as a Linux-based operating system, a Microsoft personal computer or mobile operating system, an Android operating system, an Apple mobile or personal computer operating system or other operating system. The memory module also stores location data corresponding to the location of the client device generated via user interaction with user interface, via optional Global Positioning System (GPS) receiver, one or more motion sensors such as accelerometers, gyroscopes or other sensors, or gathered via a wireless network such as triangulation data received from a 4G network, for example, location information from a connected access point or base station, femtocell or other location data. In addition, memory module includes a messaging application for communicating with other client devices such as an email application, a text, instant messaging or short messaging service (SMS) application or other messaging application that stored contacts data corresponding to users of other client devices that are known to the user of client device as well as contact information corresponding to message recipients.

The memory module also stores a data client application that is prestored in the memory module, loaded via disk or downloaded to the memory module via network interface. The delivery data client application can be a general browser application such as Mozilla, Google Chrome, Safari, Internet Explorer or other general web browser or an application that is customized to operate in conjunction with delivery data server in conjunction with the exchange of delivery data.

The processing module can be implemented via a single processing device or a plurality of processing devices. Such processing devices can include a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in a memory of memory module. The memory can include a hard disc drive or other disc drive, read-only memory, random access memory, volatile memory, non-volatile memory, static memory, dynamic memory, flash memory, cache memory, and/or any device that stores digital information. Note that when the processing device implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. While a particular bus architecture is presented that includes a single bus, other architectures are possible including additional data buses and/or direct connectivity between one or more elements. Further, the client device can include one or more additional elements that are not specifically shown.

The user device, network server, system, mobile device and other components may be part of, and/or communicate with, a network that may provide automated control of devices, appliances and other home systems (such as security systems, lighting systems, wired/wireless communication systems etc.), and may include the use of Internet of Things (IoT) technology, various input/output interfaces, Internet connectivity, and/or remote control capabilities etc., for example.

The user device, network server, system, mobile device and other components may be implemented by one or more processors or computers. It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

As may also be used herein, the terms "processor", "module", "processing circuit", and/or "processing unit" (e.g., including various modules and/or circuitries such as may be operative, implemented, and/or for encoding, for decoding, for baseband processing, etc.) may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may have an associated memory and/or an integrated memory element, which may be a single memory device, a plurality of memory devices, and/or embedded circuitry of the processing module, module, processing circuit, and/or processing unit. Such a memory device may be a read-only memory (ROM), random access memory (RAM), volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

The present invention has been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The present invention may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The above description provides specific details, such as material types and processing conditions to provide a thorough description of example embodiments. However, a person of ordinary skill in the art would understand that the embodiments may be practiced without using these specific details.

Some of the illustrative aspects of the present invention may be advantageous in solving the problems herein described and other problems not discussed which are discoverable by a skilled artisan. While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims.

Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item. Thus, the scope of the invention should be determined by the appended claims and their legal equivalents, and not by the examples given.

The invention claimed is:

1. A computer-implemented system, using a client-server model architecture, and operating as a Workplace Incident Reporting Platform (WIRP) for use by multiple user groups including at least two of an Enterprise client, a Medical facility, an Individual Associate, and an Insurance company, the system comprising:
   a WIRP Origin, an Orchestrator, and a Provisioner together defining a data servicing network;
   the WIRP Origin is configured as a server to run at least three primary services including a container registry, an identification directory, and a certificate authority;
   the WIRP Origin hosts a private Application Programming Interface (API) configured for internal operations that interact directly with data processing, data validation, data storage, and data management within the data servicing network;
   the WIRP Origin hosts a public API configured for providing authorized user groups with external access to the data servicing network;
   the Orchestrator is a container orchestration system communicatively coupled to the container registry using the WIRP Origin private API and configured to deploy, manage, store, and scale encrypted containers that contain WIRP data for permissioned access by specific user groups;
   the Provisioner is a hypervisor that provisions and manages virtual machines, the virtual machines run WIRP host node software to operate as host nodes that process WIRP data into reports, communicate data within the data servicing network utilizing the WIRP Origin private API, communicate with the identification directory in the WIRP Origin, by utilizing the WIRP Origin private API, to authorize users by authenticating user identification, and providing access to the reports via the WIRP Origin public API for an authorized user within a user group of the multiple user groups;
   the Provisioner communicates with the certificate authority in the WIRP Origin and assigns a cryptographic digital certificate to a respective host node thereby defining a valid host node, the cryptographic digital certificate is a public-key certificate that is issued by the WIRP Origin certificate authority and used to authenticate valid host nodes, which grants permissions for encrypted communications between user groups via the WIRP Origin public API, and which grants permissions for encrypted communications between the WIRP Origin, the Orchestrator, and the valid host node via the WIRP Origin private API within the data servicing network.

2. The system of claim 1, wherein the Provisioner communicates with the certificate authority in WIRP Origin to assign the cryptographic digital certificate to the host node once a virtual machine is running the WIRP host node software.

3. The system of claim 2, wherein valid host nodes are publicly accessible by authorized users in the WIRP network via the WIRP Origin public API; and wherein each host node is configured to process all incoming data from the WIRP Origin public API, and to reject any unauthorized requests.

4. The system of claim 1, wherein each host node corresponds to one of an active Enterprise client, Insurance company, and Medical facility.

5. The system of claim 1, wherein the encrypted containers include WIRP data repositories, storing the WIRP data relating to each user group, and being managed by the Orchestrator and backed-up by the WIRP Origin container registry.

6. The system of claim 5, wherein the WIRP data committed to the repositories is immutable, so that changes to a parent state of a repository require committing the changes with respect to the parent state to create a child state of the repository, which allows authorized users to see a history of changes and updates made to a respective repository; wherein updates change the saved state of the encrypted container, and saved container state changes are pushed to the WIRP Origin container registry and backed-up as a new version of the container.

7. The system of claim 6, wherein the encrypted containers are mounted to corresponding virtual machines that are operating as valid host nodes, so that the WIRP data stored in the mounted containers is available to the valid host node as a storage volume.

8. The system of claim 7, wherein changes made to the repositories from the valid host nodes affects the mounted container that includes the respective repository, so that changes made by users to WIRP data in repositories are not saved in the valid host nodes, but rather automatically saved in the mounted containers, thereby allowing the mounted containers to be unmounted from the valid host node and the data still be saved and accessible.

9. The system of claim 7, wherein valid host nodes authenticate a user's identity via the WIRP Origin identification directory upon receiving user input data via the WIRP Origin public API, process the user input data based upon a type of submitted form, and then save the processed user input data to the respective repository that is within the encrypted container mounted on the associated valid host node.

10. The system of claim 5, wherein each deployed and stored container includes tags that identify a type of WIRP data that is stored in the corresponding container; wherein branches of a WIRP data repository utilize a series of tags to allow selected WIRP data to be compartmentalized from other WIRP data; and wherein sub-branches utilize sub-tags so that a portion of the selected WIRP data can be shared with other user groups.

11. The system of claim 1, wherein data processing, data validation, data storage, and data management, within the data servicing network, are automated via the WIRP Origin private API; where requests made from the Enterprise client via the WIRP Origin public API result in automated operations via the WIRP Origin private API including creation of new repositories within encrypted containers, scaling containers, and provisioning new host nodes.

12. The system of claim 1, wherein the Orchestrator is configured to push and pull the encrypted containers to and from the WIRP Origin container registry, where the encrypted containers are backed up and version controlled for recovery and scaling; and wherein the Orchestrator is configured to scale the encrypted container's available storage and compute resources based upon the encrypted container operational needs.

13. The system of claim 1, wherein valid host nodes process WIRP data into reports including at least one of a first report of incident (FRI), a witness statement report, a personal incident report, a safety analysis report, an employee modified duty report, a medical clearance report, a workers' compensation report, an insurance report, a permission for treatment report, a drug screening report, a pandemic illness screening report, and a wellness physical report.

14. The system of claim 1, wherein the identification directory of the WIRP Origin securely stores the user identification (ID) of registered users of the user groups so that registered users can securely communicate to other registered users via the corresponding valid host node and the WIRP Origin public API.

15. The system of claim 1, wherein the WIRP Origin provides for the communication of WIRP data including videos, images, text, documents, and reports from a registered user to the Medical facility in compliance with health record portability safeguards and government regulations.

16. A computer-implemented system, using a client-server model architecture, and operating as a Workplace Incident Reporting Platform (WIRP) for use by multiple user groups including an Enterprise client, a Medical facility, an Individual Associate, and an Insurance company, the system comprising:
  a WIRP Origin, an Orchestrator, and a Provisioner together defining a data servicing network;
  wherein the WIRP Origin is configured as a server to run at least three primary services including a container registry, an identification directory, and a certificate authority;
  wherein the WIRP Origin hosts a private Application Programming Interface (API) configured for internal operations that interact directly with data processing, data validation, data storage, and data management within the data servicing network;
  wherein the WIRP Origin hosts a public API configured for providing authorized user groups with external access to the data servicing network;
  wherein the Orchestrator is a container orchestration system communicatively coupled to the container registry using the WIRP Origin private API and configured to deploy, manage, and store encrypted containers that contain WIRP data for permissioned access by specific user groups;
  wherein the WIRP Origin provides for the communication of WIRP data including videos, images, text, documents, and reports from a registered user of the user groups to the Medical facility in compliance with health record portability safeguards and government regulations;
  wherein the Provisioner is a hypervisor that Provisions and manages virtual machines, the virtual machines run WIRP host node software to operate as host nodes that process WIRP data, communicate data within the data servicing network utilizing the WIRP Origin private API, communicate with the identification directory to authorize users by authenticating user identification, and providing access to the WIRP data via the WIRP Origin public API for an authorized user within a user group of the multiple user groups;
  wherein each host node corresponds to one of an active Enterprise client, Insurance company, and Medical facility;
  wherein valid host nodes process WIRP data into reports including at least one of a First Report of Injury (FRI), a witness statement report, a personal incident report, a safety analysis report, an employee modified duty report, a medical clearance report, a workers comp report, an insurance report, a permission for treatment report, a drug screening report, a pandemic illness screening report, and a wellness physical report; and
  wherein the Provisioner communicates with the certificate authority and assigns a cryptographic digital certificate to a respective host node thereby defining a valid host node with respect to an Enterprise client, which thereby grants permissions for encrypted communications between user groups via the WIRP Origin public API, and which grants permissions for encrypted communications between the WIRP Origin, the Orchestrator, and the valid host node via the WIRP Origin private API within the data servicing network.

17. The system of claim 16, wherein the Provisioner communicates with the certificate authority in WIRP Origin to assign the cryptographic digital certificate to the host node once a virtual machine is operating as a host node; and wherein valid host nodes are publicly accessible by authorized users in the WIRP network via the WIRP Origin public API; and wherein each host node is configured to process all incoming data from the WIRP Origin public API, and to reject any unauthorized requests.

18. The system of claim 16, wherein the encrypted containers include WIRP data repositories, storing the WIRP data relating to each user group, and being managed by the Orchestrator and backed-up by the WIRP Origin container registry; wherein the WIRP data committed to the repositories is immutable, so that changes to a parent state of a repository require committing the changes with respect to the parent state to create a child state of the repository, which allows authorized users to see a history of changes and updates made to a respective repository; wherein updates change the saved state of the encrypted container, and saved container state changes are pushed to the WIRP Origin container registry and backed-up as a new version of the container; wherein the encrypted containers are mounted to corresponding virtual machines that are operating as valid host nodes, so that the WIRP data stored in the mounted containers is available to the valid host node as a storage volume.

19. The system of claim 18, wherein changes made to the repositories from the valid host nodes affects the mounted container that includes the respective repository, so that changes made by users to WIRP data in repositories is not saved in the valid host nodes, but rather automatically saved in the mounted containers, thereby allowing the mounted containers to be unmounted from the valid host node and the data still be saved and accessible.

20. The system of claim 18, wherein valid host nodes authenticate a user's identity via the WIRP Origin identification directory upon receiving user input data via the WIRP Origin public API, process the user input data based upon a type of submitted form, and then save the processed user input data to the respective repository that is within the encrypted container mounted on the associated valid host node.

21. The system of claim 18, wherein each deployed and stored container includes tags that identify a type of WIRP data that is stored in the corresponding container; wherein branches of a WIRP data repository utilize a series of tags to allow selected WIRP data to be compartmentalized from other WIRP data; and wherein sub-branches utilize sub-tags so that a portion of the selected WIRP data can be shared with other user groups.

22. The system of claim 16, wherein data processing, data validation, data storage, and data management, within the data servicing network, are automated via the WIRP Origin private API; where requests made from the Enterprise client via the WIRP Origin public API result in automated operations via the WIRP Origin private API including creation of new repositories within encrypted containers, scaling containers, and provisioning new host nodes.

23. The system of claim 16, wherein the Orchestrator is configured to push and pull the encrypted containers to and from the WIRP Origin container registry, where the encrypted containers are backed up and version controlled for recovery and scaling; and wherein the Orchestrator is configured to scale the encrypted container's available storage and compute resources based upon the encrypted container operational needs.

* * * * *